United States Patent [19]

Lu

[11] Patent Number: 5,792,192
[45] Date of Patent: Aug. 11, 1998

[54] PACEMAKER WITH AUTOMATIC MODE SWITCHING USING DETECTION OF HIDDEN INTRINSIC CARDIAC PULSES

[76] Inventor: Richard Lu, 9917 S. Spring Hill La., Highlands Ranch, Colo. 80126

[21] Appl. No.: 843,633

[22] Filed: Apr. 19, 1997

[51] Int. Cl.$^6$ .................................................. A61N 1/362
[52] U.S. Cl. .......................................................... 607/14
[58] Field of Search ............................ 607/9, 14, 15, 607/17

[56] References Cited

U.S. PATENT DOCUMENTS

| | | |
|---|---|---|
| 4,702,253 | 10/1987 | Nappholz et al. . |
| 4,766,901 | 8/1988 | Callaghan . |
| 4,901,725 | 2/1990 | Nappholz et al. . |
| 4,974,589 | 12/1990 | Sholder ........................ 607/9 |
| 5,342,405 | 8/1994 | Duncan ....................... 607/14 |
| 5,441,523 | 8/1995 | Nappholz . |
| 5,658,320 | 8/1997 | Betzold et al. ............... 607/14 |

*Primary Examiner*—William E. Kamm
*Attorney, Agent, or Firm*—Gottlieb, Rackman & Reisman, P.C.

[57] ABSTRACT

In a rate responsive pacemaker, an AMS (automatic mode switching) feature is selectively turned on or off depending on whether atrial tachycardia is present. An atrial tachycardia condition is recognized by analyzing a pattern of short and long atrial event intervals. The pattern may be changed by adjusting a pacing parameter such as a maximum ventricular pacing rate. The pattern changes because by changing the pacing parameters, some of the atrial events are uncovered which have been previously hidden or masked by blanking periods, especially the cross channel atrial blanking period.

22 Claims, 29 Drawing Sheets

PACEMAKER WITH AUTOMATIC MODE SWITCHING USING DETECTION OF HIDDEN INTRINSIC CARDIAC PULSES

BACKGROUND OF THE INVENTION

1. Field of the Invention

This invention relates to dual chamber pacemakers, and more particularly, to a mode of operation wherein intrinsic cardiac activity in one or more cardiac chambers are monitored and if no intrinsic activity is sensed then, after a preset duration, the chamber is paced.

2. Description of the Prior Art

Conventional pacemakers operating, for example, in a DDDX mode are normally provided with means for sensing and pacing both the atrium and the ventricle. Typically, in these types of devices, if an intrinsic or pacing pulse occurs in one of the chambers, for example, the atrium, then this activity may be erroneously sensed in the other chamber due to cross talk. In order to eliminate this source of error, in the past, pacemakers have been provided with blanking periods for blanking the sensor in one channel after a cardiac pulse occurs in the other. This blanking period is usually referred to as the cross-channel blanking period. Pacemakers may also be provided with in-channel blanking periods, which may be of no interest to the present invention. Following the blanking period, an alert period is designated during which the cardiac chamber of interest is monitored for intrinsic activity. If no such activity is sensed by the end of this alert channel, then a pacing pulse is applied to the chamber. One such pacemaker is described in commonly assigned U.S. Pat. No. 5,441,523, and incorporated herein by reference.

Some pacemakers are also provided with an Automatic Mode Switching (AMS) feature which is designed to overcome the limitations of conventional dual chamber pacemakers in the presence of atrial tachyarrhythmias. When AMS is enabled, the pacemaker will automatically switch from a dual chamber mode to a ventricular pacing mode upon the detection of a fast atrial rhythm to avoid rapid ventricular tracking. For example, in the Telectronics models 1256 and 2102, available from Telectronics of Englewood, Colorado, AMS is implemented by providing two programmable parameters designated AMS Rate and AMS Count. The parameter AMS Rate sets the upper boundary of a tracked atrial rate. If an atrial rate above this parameter is sensed, the AMS mode is enabled. The parameter AMS Count sets the number of intervals that must exceed the AMS detection rate before AMS occurs. Sensed atrial rates above the AMS Rate cause the mode switching to be effected, but if and only if the number of atrial events in a pre-determined interval, such as 150 bpm, exceeds the AMS Count parameter. The parameter AMS Rate is programmable from 130–200 bpm in steps of 10 bpm or it can be set OFF (to disable the AMS function). AMS Count is programmable from 3 to 11 counts in steps of 1. AMS is controlled by an atrial rate monitor as described more fully below. The atrial rate monitor counts intervals between atrial events. In order to control the duration during which AMS is activated, the atrial rate monitor uses two counters: a short interval counter that triggers AMS and a long interval counter that ends AMS operation. When AMS is enabled, every short atrial interval increases the short interval counter and every long interval decreases the short interval counter. If the short interval counter counts up to the programmed AMS Count, AMS occurs. After AMS is initiated, the long interval counter is activated. Every long interval increases the long interval counter and every short interval decreases the long interval counter. When the long interval counter reaches a preset number, such as three, or if no atrial event is sensed for 1 second, the AMS feature is terminated and dual chamber operation resumes.

To detect a fast atrial rhythm for AMS to function properly, fast atrial beats must be sensed appropriately. However, atrial beats cannot be sensed if they fall inside the blanking periods or are under-sensed. The former can happen when there is a stable atrial tachyarrhythmia (e.g., atrial flutter) in which some or all of every other atrial beat fall inside the postventricular atrial blanking period. If all of every other atrial beat fall inside the blanking period, a stable 2:1 tracking rate in the ventricle may result. This should not be a concern if the ventricular rate is not too high. However, if some of every other atrial beat falls inside the blanking period, an unstable tracking rate in the ventricle may be in effect. This may cause patient discomfort. Under-sensing in the atrial channel happens more often during episodes of low amplitude atrial fibrillation. Inappropriate atrial sensing of atrial tachyarrhythmias can result in inappropriate ventricular tracking of the atrial rhythm or intermittent mode switching. Intermittent mode switching may potentially cause patient discomfort.

OBJECTIVES AND SUMMARY OF THE INVENTION

In view of the disadvantages of the prior art, it is an objective of the present invention to provide a pacemaker in which an AMS feature is provided which has an improved sensitivity to detect atrial tachyarrhythmias.

A further objective is to provide a pacemaker which can detect atrial events masked within an in-channel or cross-channel blanking period, said masked atrial events being used to enable an AMS feature.

Yet a further objective is to provide a pacemaker with an asymmetrical atrial counter for controlling the triggering of an AMS feature.

Other objectives and advantages of the invention shall become apparent from the following description. Briefly, a pacemaker constructed in accordance with this invention includes sensors for sensing cardiac activity, pacing generators for generating pacing pulses to the cardiac chambers, a metabolic rate generator for generating a metabolic indicated rate, a controller for controlling the generators in accordance with said cardiac activities and said metabolic indicated rate and an AMS controller for generating an AMS signal to override the operation of said controller. The AMS controller detects abnormal atrial activity.

In one embodiment, hidden atrial beats in the blanking period are exposed so that the presence of an atrial tachyarrhythmia can be confirmed. A second embodiment makes use of asymmetrical counters to improve the sensitivity of an atrial tachyarrhythmia detection when intermittent under-sensing in the atrium occurs.

BRIEF DESCRIPTION OF THE DRAWINGS

Further objectives, features and advantages of the invention will become apparent upon consideration of the following description, taken in conjunction with the accompanying drawing, in which.

DETAILED DESCRIPTION OF THE INVENTION

Figure 1:
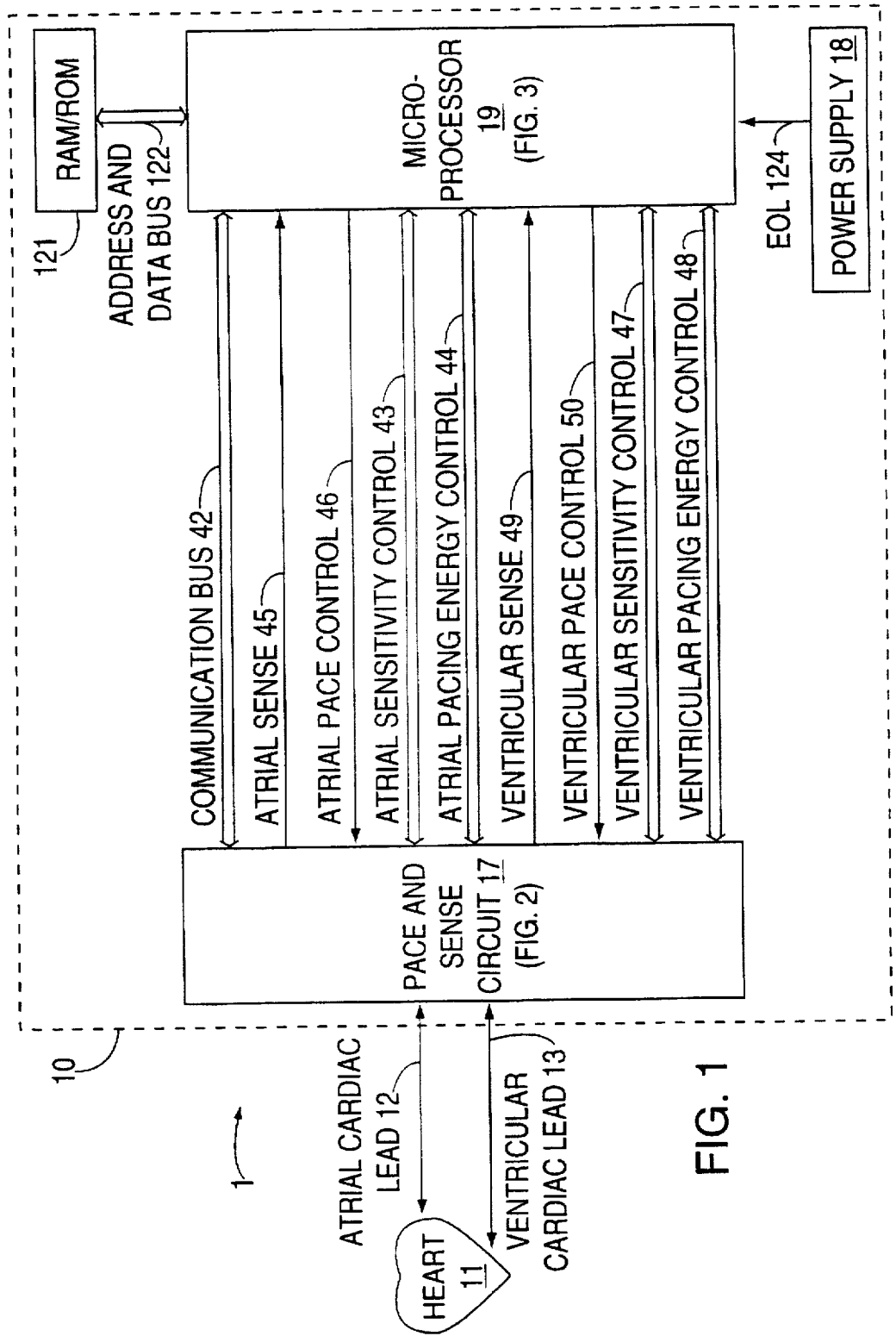
FIG. 1 is a block diagram of a rate-responsive, dual chamber pacemaker which embodies the subject invention.

FIG. 1 shows a block diagram of a pacemaker 1. The pacemaker 1 is designed to be implanted in a patient and includes a pulse generator 10 and appropriate leads for electrically connecting the pulse generator to a patient's heart 11. The pacemaker includes an atrial cardiac lead 12 extending to the atrium of the patient's heart for the administration of pacing therapy to the atrium, and a ventricular cardiac lead 13 extending to the ventricle of the patient's heart for the administration of pacing therapy to the ventricle. The pulse generator 10 includes a pace and sense circuit 17 for the detection of analog signals representing cardiac electrical activity and for the delivery of pacing pulses to the heart; a microprocessor 19 which, in response to numerous inputs received from the pace and sense circuit 17, performs operations to generate different control and data outputs to the pace and sense circuit 17; and a power supply 18 which provides a reliable voltage level to the pace and sense circuit 17 and the microprocessor 19 by electrical conductors (not shown).

The microprocessor 19 is connected to a random access memory/read only memory unit 121 by an address and data bus 122. An end-of-life signal line 124 is used to provide, to the microprocessor 19, a logic signal indicative of the approach of battery failure in the power supply 18. The microprocessor 19 and the pace and sense circuit 17 are connected by a communication bus 42, an atrial sense line 45, an atrial pacing control line 46, an atrial sensitivity control bus 43, an atrial pace energy control bus 44, a ventricular sense line 49, a ventricular pace control line 50, a ventricular sensitivity control bus 47, and a ventricular pacing energy control bus 48.

Figure 2:
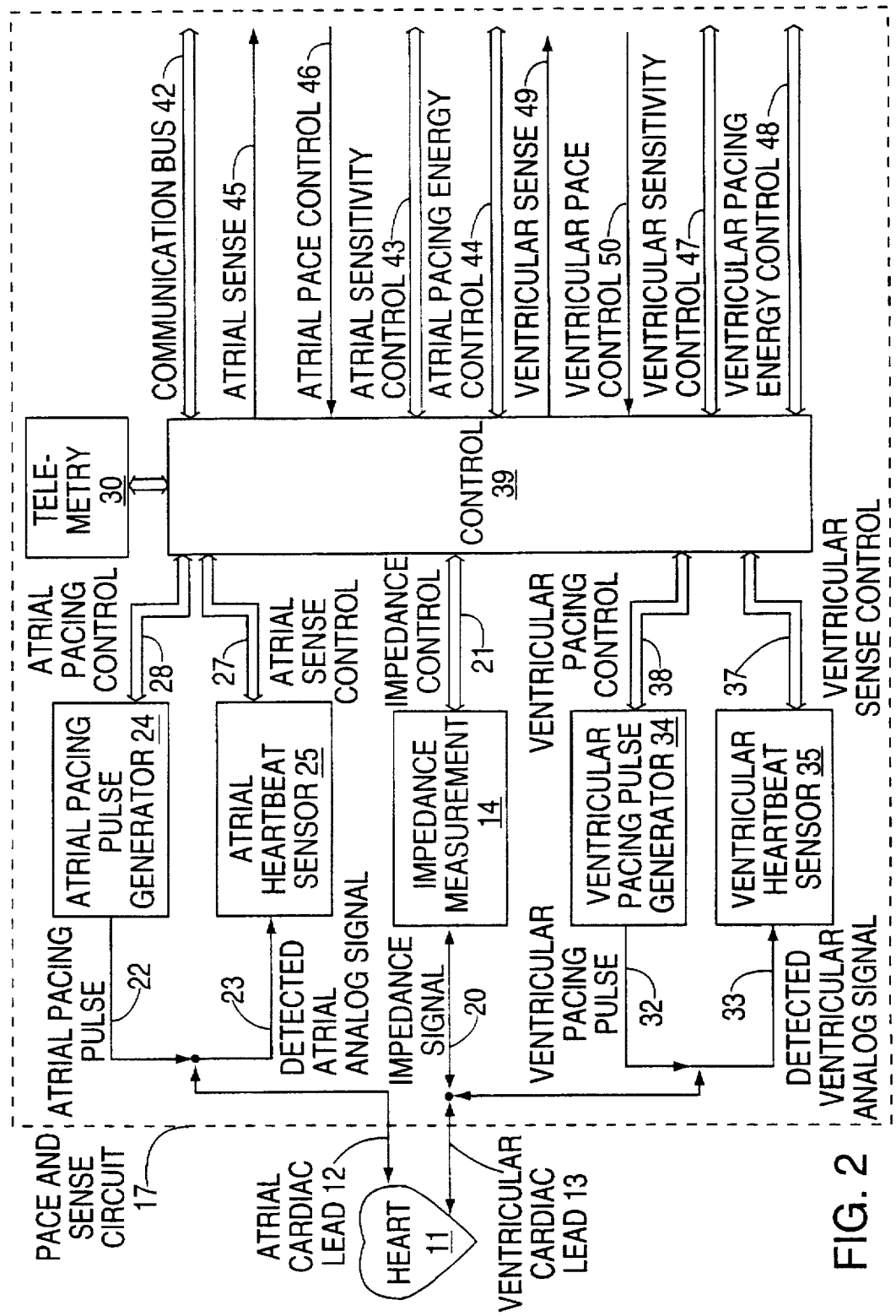
FIG. 2 is a block diagram of the pace and sense circuit 17 of FIG. 1.

FIG. 2 shows the pace and sense circuit 17 which includes circuitry for an atrial pacing pulse generator 24, a ventricular pacing pulse generator 34, an atrial heartbeat sensor 25, a ventricular heartbeat sensor 35, and a telemetry circuit 30. The preferred embodiment of the pace and sense circuit 17 includes an impedance measurement circuit 14 for measuring a physiological parameter indicative of the patient's metabolic demand. Also, the pace and sense circuit 17 includes a control block 39 which has an interface to the microprocessor 19.

In operation, the atrial and ventricular heartbeat sensor circuits 25 and 35 detect respective atrial and ventricular analog signals 23 and 33 from the heart 11 and convert the detected analog signals to digital signals. In addition, the heartbeat sensor circuits 25 and 35 receive an input atrial sense control 27 and an input ventricular sense control 37, respectively, from the control block 39 which determines the sensitivities of the sensor circuits. The sensitivity determines the minimum voltage deviation required at a sensing electrode for a sense to be registered, i.e., a depolarization signal to be recognized by the pacemaker.

The atrial pacing pulse generator circuit 24 receives from the control block 39, via an atrial pacing control bus 28, an atrial pace control input and an atrial pacing energy control input to generate an atrial pacing pulse 22 [A-pace] at appropriate times. Similarly, the ventricular pacing pulse generator circuit 34 receives from the control block 39, via a ventricular pacing control bus 38, a ventricular pace control input and a ventricular pacing energy control input to generate a ventricular pacing pulse [V-pace] 32. The atrial and ventricular pace control inputs determine the respective types of atrial and ventricular pacing that take place, while the atrial and ventricular pacing energy control inputs determine the respective magnitudes of the pulse energies.

The pacemaker 1 makes an impedance measurement when the microprocessor 19 sends a signal on the impedance control bus 21 to activate the impedance measurement circuit 14. The impedance measurement circuit 14 then applies a current to the ventricular cardiac lead 13 and measures a voltage resulting from the applied current to monitor the impedance. The current and voltage signals jointly are termed an impedance signal 20.

The telemetry circuit 30 provides a bidirectional link between the control block 39 of the pace and sense circuit 17 and an external device such as a programmer. It allows data such as the operating parameters to be read from or altered in the implanted pacemaker. An exemplary programmer is the 9600 Network Programmer manufactured by Telectronics of Englewood, Colo., U.S.A.

Figure 3:
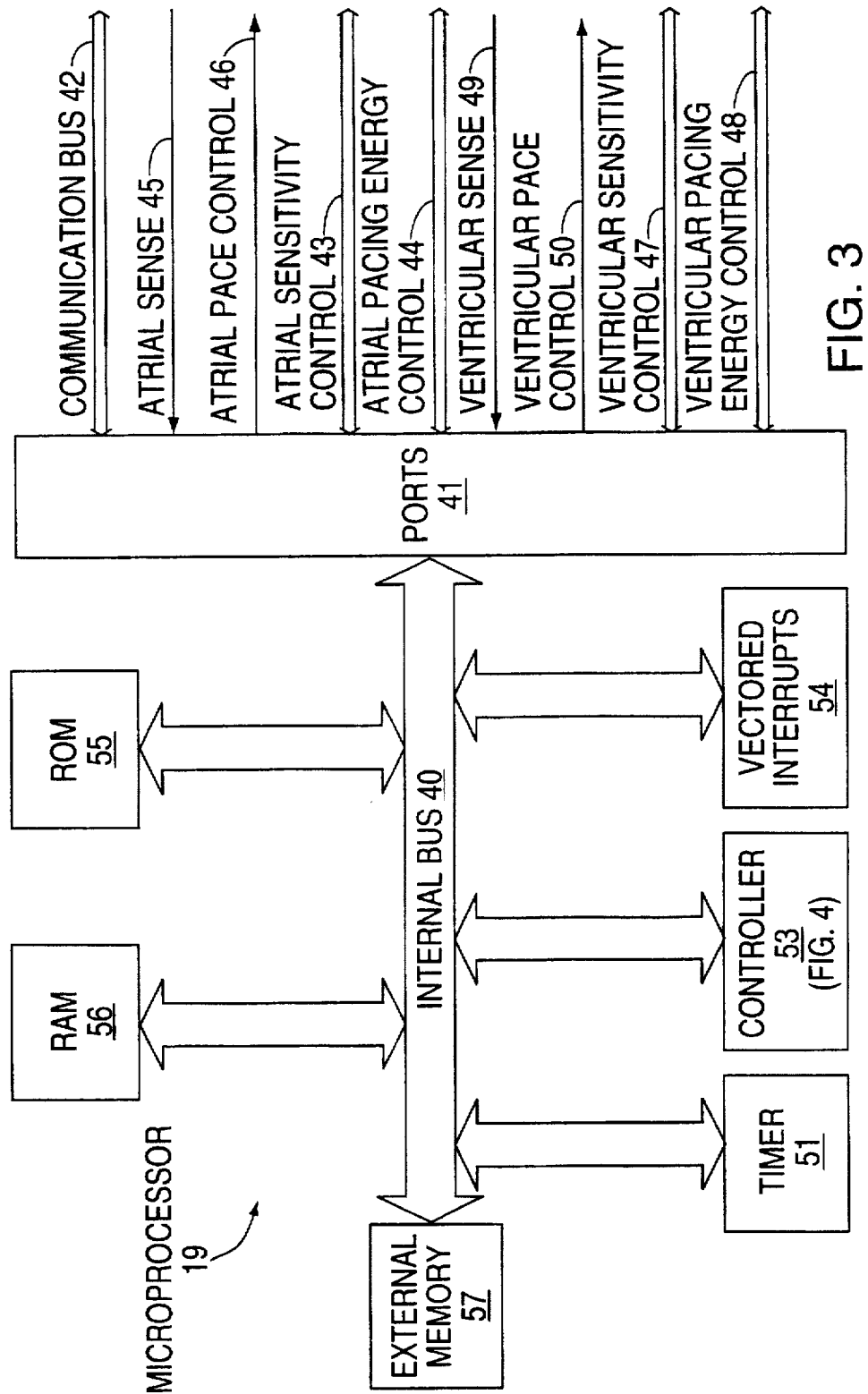
FIG. 3 is a block diagram of the microprocessor of FIG. 1.

FIG. 3 shows the microprocessor 19 as comprising a timer circuit 51 which may include multiple individual 16-bit timer circuits, a controller 53, a vectored interrupts block 54, a ROM 55, a RAM 56, an external memory 57 and a ports block 41. These circuits mutually communicate using an internal communications bus 40. The RAM 56 acts as a scratch pad and active memory during execution of the programs stored in the ROM 55 and used by the microprocessor 19. These programs include system supervisory programs, detection algorithms for detecting and confirming arrhythmias, and programming for implementing various pacemaker functions, as well as storage programs for storing, in external memory 57, data concerning the functioning of the pulse generator 10 and the electrogram provided by the ventricular cardiac lead 13. The timers 51, and their associated control software, implement some timing functions required by the microprocessor 19 without resort entirely to software, thus reducing computational loads on, and power dissipation by, the controller 53.

Signals received from the telemetry circuit 30 permit an external programmer (not shown) to change the operating parameters of the pace and sense circuit 17 by supplying appropriate signals to the control block 39. The communications bus 42 serves to provide signals indicative of such control to the microprocessor 19.

Appropriate telemetry commands will cause the telemetry circuit 30 to transmit data to the external programmer. Data stored is read out, by the microprocessor 19, on to the communications bus 42, through the control block 39 in the pace and sense circuit 17, and into the telemetry circuit 30 for transmission to the external programmer by a transmitter in the telemetry circuit 30.

The microprocessor 19 through its ports block 41 receives status and/or control inputs from the pace and sense circuit 17, such as the sense signals on the sense lines 45 and 49. It performs operations, including arrhythmia detection, and produces outputs, such as the atrial pace control on the line 46 and the ventricular pace control on the line 50, which determine the type of pacing that is to take place. Other control outputs generated by the microprocessor 19 include the atrial and ventricular pacing energy controls on the buses 44 and 48, respectively, which determine the magnitude of the pulse energy, and the atrial and ventricular sensitivity controls on the buses 43 and 47, respectively, which set the sensitivities of the sensing circuits.

The pacemaker 1 may employ a metabolic sensor to distinguish whether atrial heartbeats are occurring at a physiological rate or a pathological rate. The pacemaker 1 responds to a physiological atrial rate by functioning in an AV synchronous pacing mode with pacing pulses in the ventricle delivered at a predetermined interval following an atrial heartbeat. When the pacemaker 1 detects a pathological atrial rate, it responds by functioning in a forced synchrony mode of operation. A metabolic sensor system, which is suitable for operation in the present invention, may be made up of one or more known sensors either solely or in combination with other sensors, including but not limited to minute volume, ventricular depolarization gradient, QT-interval, oxygen saturation, pH, central venous blood temperature, right ventricular pressure, stroke volume, systolic time intervals, respiration rate and ultrasonic or pressure monitoring of cardiac output. The pacemaker 1 of the present invention will function properly using any metabolic indicator rate system, so long as that system is able to reliably relate the sensed parameter to a metabolic demand pacing rate. U.S. Pat. No. 4,766,901, to F. Callaghan, issued Aug. 30, 1988, for "Rate Responsive Pacing System Using the Integrated Evoked Potential," refers to the operation of a rate-responsive pacing system using an integrated evoked ventricle depolarization potential as a metabolic demand pacing rate indicator. U.S. Pat. No. 4,702,253 to T. Nappholz et al., issued Oct. 27, 1987, for "Metabolic-Demand Pacemaker and Method of Using the Same to Determine Minute Volume," and U.S. Pat. No. 4,901,725, to T. Nappholz, et al., issued Feb. 20, 1990 for "Minute Volume Rate-Responsive Pacemaker", disclose rate-responsive pacers describing another metabolic demand pacing rate indicator, respiratory minute volume, as the rate control parameter. The above-mentioned patents are hereby incorporated by reference. The preferred embodiment of the invention employs an impedance sensor 14, shown in FIG. 2 which may perform the respiratory minute volume measurements of the Nappholz, et al. patents.

Figure 4:
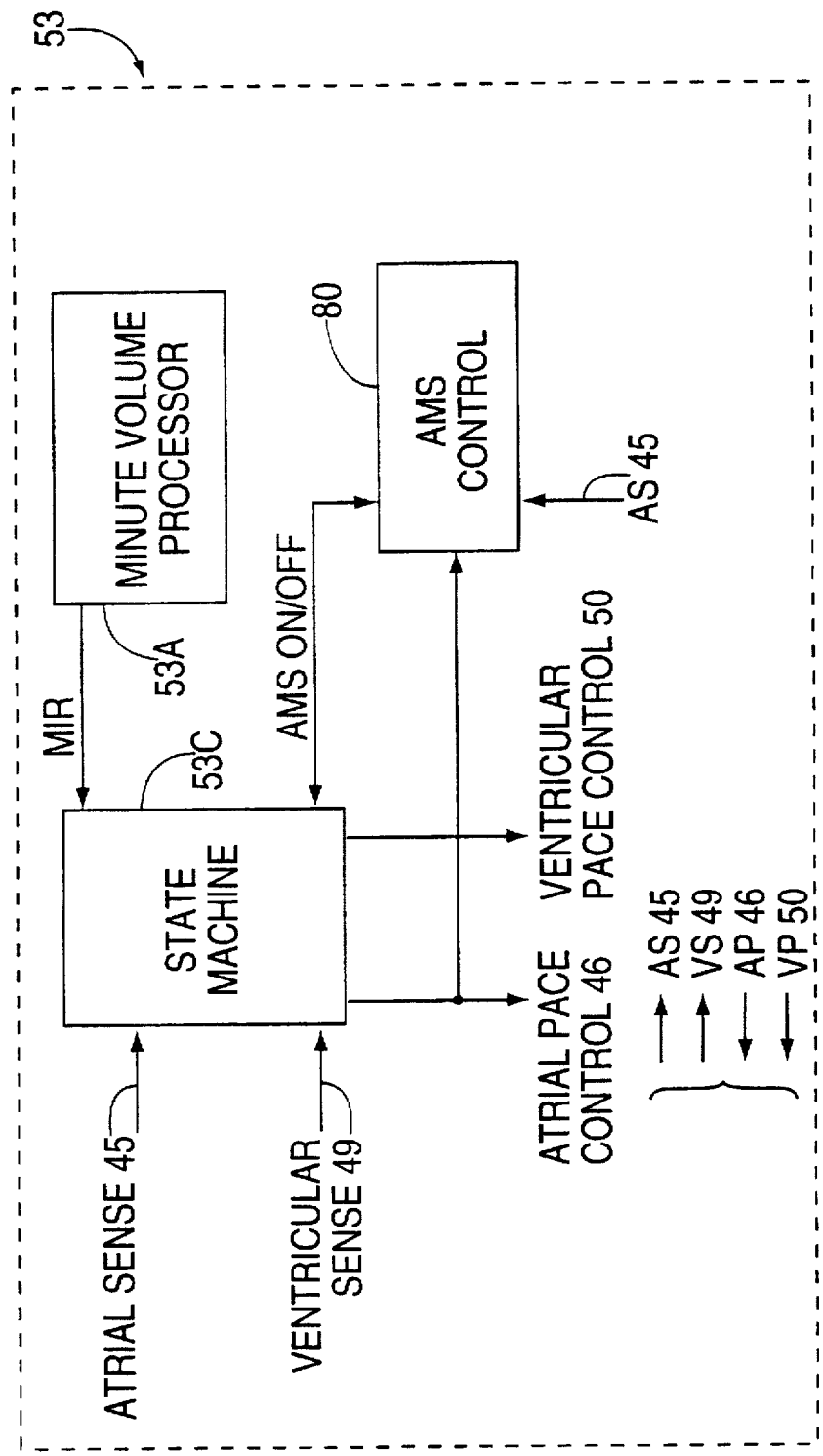
FIG. 4 is a functional block diagram of the controller of FIG. 3.

FIG. 4 shows the functional block diagram of the controller 53 of FIG. 3. The minute volume processor 53A uses the data supplied via the internal bus 40 and the communication bus 42 from the impedance measurement block 14 to generate the Metabolic Indicated Rate Interval (MIR) which is used by the pacing and sensing system (shown symbolically as the "DDD pacer block 53C in FIG. 4) to determine the length of each of the intervals used in the timing cycle. The AMS controller 80 monitors the atrial rate and generates an AMS on/off signal to the state machine 53C. When this AMS signal is off, the state machine generates atrial and ventricular pacing signals on demand and in synchrony, as described in U.S. Pat. No. 5,441,523. If the AMS signal is on, then the state machine overrides the MIR rates and operates at a fall back rate which is a programmable parameter stored in the AMS control circuit 80. This mode continues until the AMS control signal is turned off.

Figure 4A:
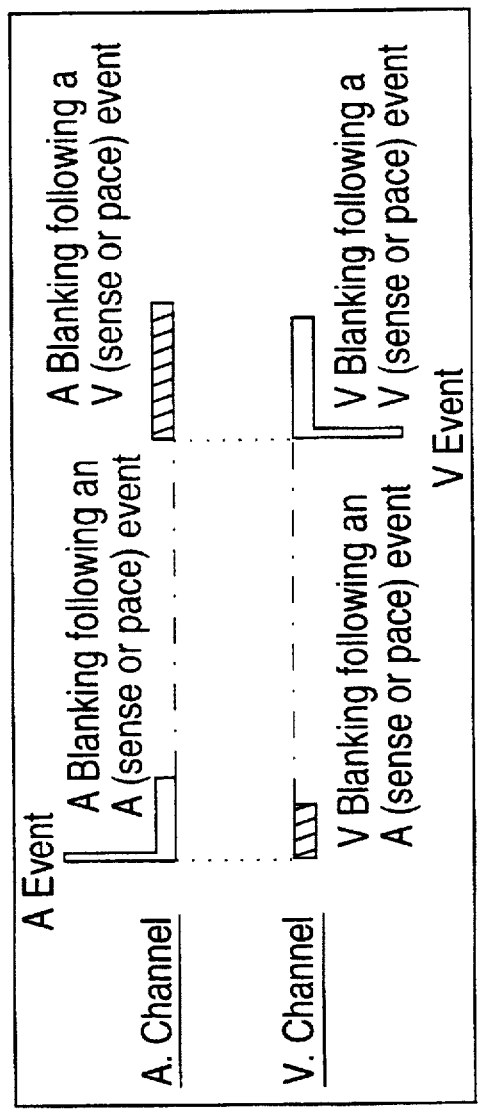
FIG. 4A shows a timing diagram with the various blanking periods.

The sensing amplifier of all pacemakers disables its sensing ability for a brief period following a sensed or a paced event. The time during which sensing is disabled is called a blanking period. The blanking period prevents inappropriate sensing from the pacemaker amplifier following an intrinsic event or a pacemaker output pulse. The blanking period may be applied to the same chamber where the event occurs. In dual chamber pacemakers, the blanking period also may be applied to the chamber other than the one in which the event occurs. In this case, the blanking period is called the cross-channel blanking period. There are eight possible blanking periods (See FIG. 4A) in a pacemaker:

(1) atrial blanking period after an atrial sense, (2) atrial blanking period after an atrial pace, (3) atrial blanking period after a ventricular sense, (4) atrial blanking period after a ventricular pace, (5) ventricular blanking period after an atrial sense, (6) ventricular blanking period after an atrial pace, (7) ventricular blanking period after a ventricular sense, and (8) ventricular blanking period after a ventricular pace.

It should be noted that the ventricular blanking period after an atrial sense (5) in some pacemakers is turned off.

Conventionally, the blanking period is a fixed interval that is designed to prevent inappropriate sensing under any combination of the following programmed parameters which may affect the sensing functions of a pacemaker: sensing/pacing polarity, sensitivity, pacing amplitude, pulse width and possibly other lead factors. In general, the fixed blanking period is conservatively set for the worst case of these parameter settings.

In a pacemaker with Automatic Mode Switching (AMS) function, the sensitivity of AMS detection may be reduced due to unnecessarily long blanking periods in the atrial channel. Hidden atrial senses may occur if the events fall inside the atrial blanking period following an atrial (sensed or paced) event or the atrial blanking period following, a ventricular (sensed or paced) event. It is less likely that atrial beats fall inside the atrial blanking period following an atrial (sensed or paced) event since this period is usually short (e.g., 100–120 ms) and occurs right after the atrial event. It is more often that hidden senses fall inside the cross-channel blanking period following a ventricular paced event. The worst case is when the operating AV delay is equal to or shorter than the atrial blanking period following an atrial event (this may happen more often with the availability of adaptive AV delay). In this case, the atrial blanking period will be extended by the cross-channel blanking period following a ventricular paced event at the end of the operating AV delay. Potentially, fast and stable atrial events fall inside this period, atrial blanking period cannot be sensed and the atrial tachycardia is not detected. In general, some or all of every other atrial beats fall inside the postventricular atrial blanking period if:

Operating AV Delay $\leq$ tachycardia cycle length $\leq$ Operating AV Delay+postventricular atrial blanking period A stable atrial tachyarrhythmia is detected if either:

(1) there is a pattern of some long-sensed intervals followed by some short-sensed intervals where the cycle length of the short interval is approximately 50% of the long interval, the short interval falls inside the postventricular atrial blanking period and is shorter than the cycle length of the programmed AMS Rate; or (2) there is a stable pattern of atrial sensed events where 50% of the sensed atrial cycle length would fall inside the postventricular atrial blanking period, the interval that is 50% of the sensed cycle length is shorter than the interval of the programmed AMS Rate and twice the rate of the sensed cycle length and is a certain percentage (e.g., 30%) higher than the current sensor indicated rate.

Figure 8:
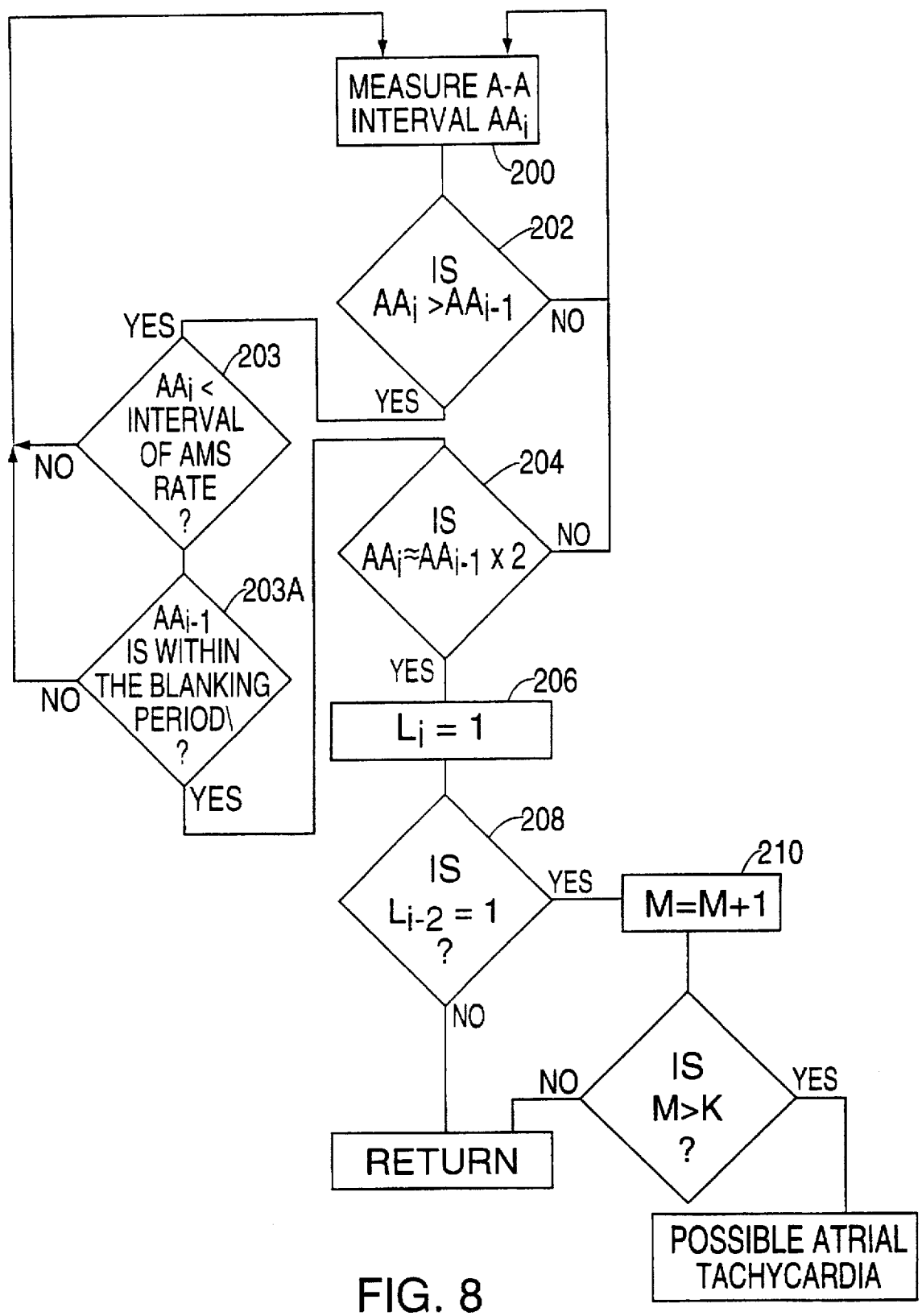
FIG. 8 shows a flow chart for a first embodiment of the invention.
Figure 11:
FIG. 11 shows a pattern of short and long atrial events indicative of possible atrial tachyarrhythmia for the embodiment of FIG. 8.

FIG. 8 shows a flowchart for performing the first detection criteria. For this chart it is assumed that every second atrial intrinsic signal is hidden and therefore a pattern of SLSLSLSL . . . occurs where each S indicates a short A—A interval and each L indicates a long interval with an intrinsic hidden atrial event. Under these conditions, each L is about twice as long as an S interval. This pattern is shown in FIG. 11 and is detected as follows: In step 200 the current A—A interval, designated as $AA_i$ is measured. In step 202 this parameter is compared to the immediately preceding interval $AA_{i-1}$. The purpose of this step is to determine whether the current A—A interval is a long interval because of a hidden intrinsic atrial event. If in step 202 it is found that this interval is longer, then in step 203 a test is performed to check if the interval $AA_{i-1}$ is shorter than the interval corresponding to the AMS rate. The AMS rate is a programmed parameter, as mentioned above. If it is, then in step 203A a test is performed to determine if $AA_{i-1}$ is within the blanking period. If it is, then in step 204 a test is performed to determine if the latest interval is about twice as long as the preceding interval. If it is not, then atrial tachycardia is not suspected. If it is, then in step 206 an arbitrary parameter $L_i$ is set to '1' to indicate that an SL occurrence has been detected. In step 208 a check is performed to determine if the interval i-2 also conforms to the SL pattern, i.e., whether $L_{i-2}$ is equal to 1. For the first time around, i.e., at the beginning of the pattern, this test is negative. The test continues for the next S and L intervals. For the second L interval the step 208 is positive and therefore in step 210 a second parameter M is incremented. M counts the number of successive SL occurrences in the pattern. In step 212 the parameter M is compared to a preset threshold K which sets the number of sequences SL in the whole pattern required to determine that atrial tachycardia is taking place. If M exceeds K, then atrial tachycardia is indicated, otherwise the test continues.

Figure 9:
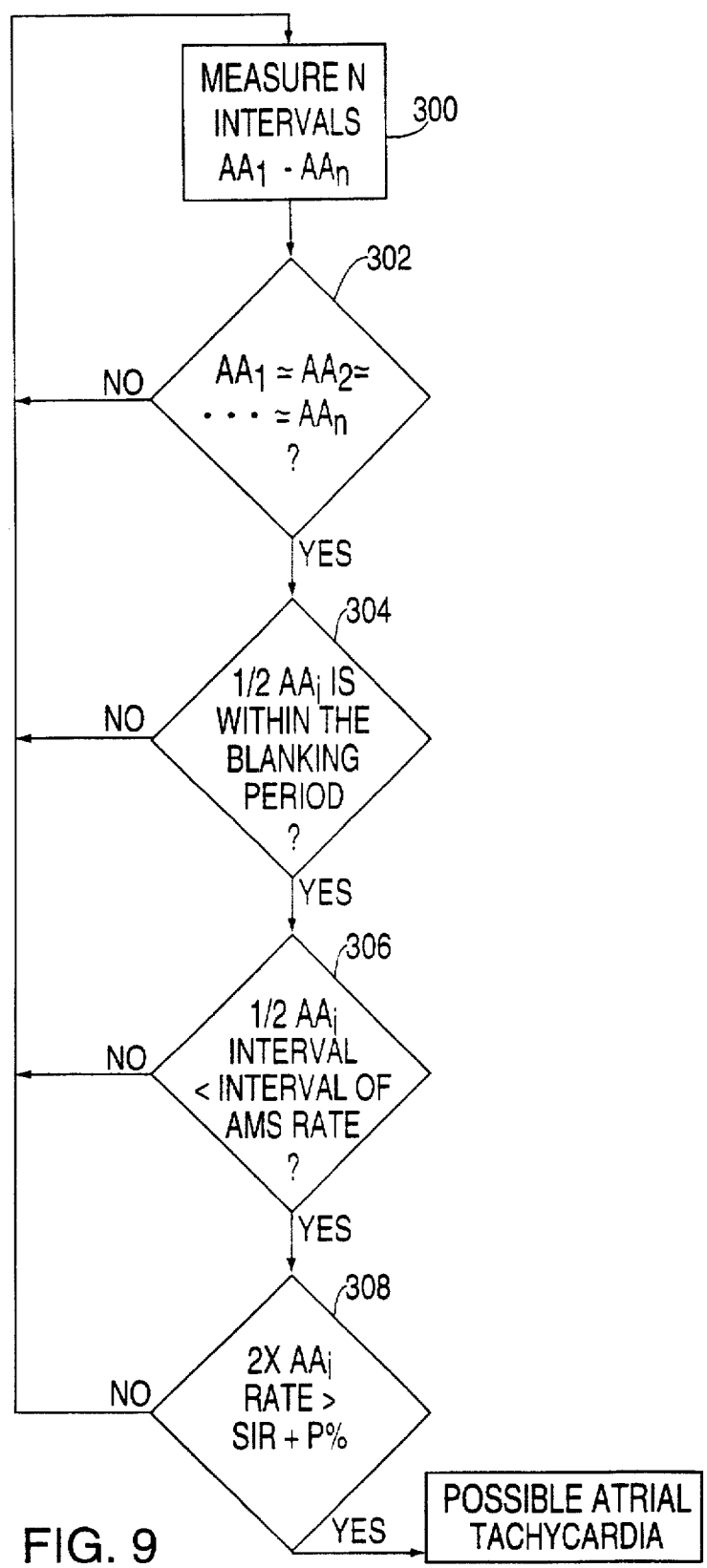
FIG. 9 shows a flow chart for a second embodiment of the invention.

A flowchart for the second detection criteria is shown in FIG. 9. In this flowchart it is assumed that the atrial-sensed events are somewhat stable and long (because every other intrinsic atrial event is hidden in the blanking period). In FIG. 9, step 300 the N intervals $AA_i$–$AA_n$ are measured. In step 302, a test is conducted to determine whether the last n atrial sensed events are about the same. If this test is positive, then step 304 tests if half of the $AA_i$ intervals are within the blanking period. Step 306 tests if half of the $AA_i$ are intervals are less than the AMS rate interval. Step 308 tests if twice the rate of $AA_i$ interval exceeds the Sensor Indicated Rate (SIR) by a percentage P. For example, P may be about 30%. If this test 308 is positive, then a possible atrial tachycardia is indicated.

Figure 10:
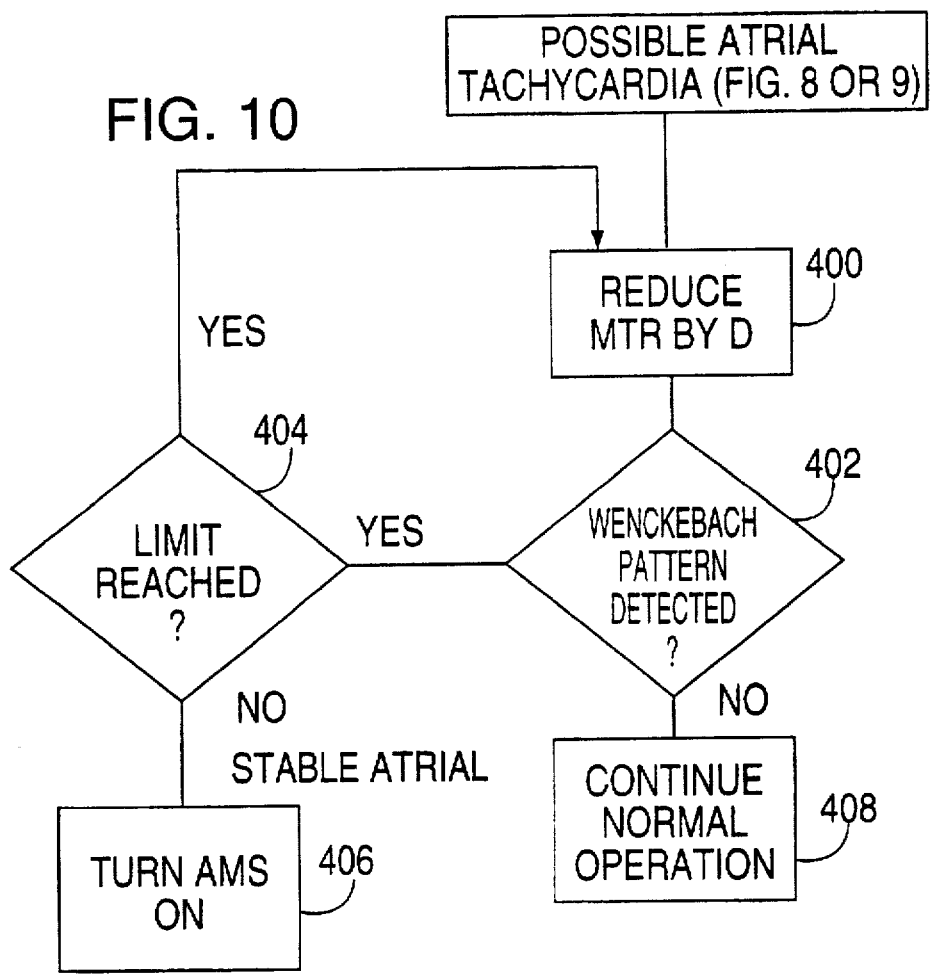
FIG. 10 shows a flow chart showing how a possible atrial tachyarrhythmia (e.g., atrial flutter) state is confirmed.
Figure 12:
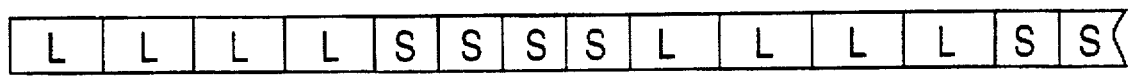
FIG. 12 shows a pattern of long and short atrial events characteristic of Wenckebach behavior and used for the confirmation feature of FIG. 10.

If either of the two tests of FIGS. 8 or 9 indicates a possible atrial tachycardia, i.e., one of the detection criteria is met, a confirmation process is performed (FIG. 10). The Maximum Tracking Rate (MTR) is automatically reduced from an initial value (step 400) by a few beats D. (e.g., 5 ppm). MTR determines the maximum atrial rate that is tracked in the ventricle. The slower MTR will force the pacemaker to develop Wenckebach behavior. This behavior is characterized by a pattern of some long atrial sensed intervals followed by some short atrial sensed intervals. For example, this pattern may have the form of LLLLSSSS . . . This pattern is illustrated in FIG. 12. In step 402, the next N atrial activities are monitored to see if the Wenckebach pattern is detected. If the pattern is detected, the MTR will continue to be reduced slowly by a few beats (e.g., 5 ppm) at a time until it reaches the sensor indicated rate (MIR) (if available) or a low preselected threshold rate is reached (step 404). This low rate is typically 70 ppm. If a pattern of long intervals followed by some short intervals is observed at each reduced MTR, then the presence of a stable atrial tachyarrhythmia is confirmed and AMS is turned on (step 406). At any tested MTR throughout this confirmation process, the presence of a stable atrial tachyarrhythmia is not confirmed if a pattern of some long intervals followed by some short intervals with the short interval faster than the AMS Rate is not seen (step 402). In this case, AMS is not turned on and the MTR is changed back to its operational value or the originally programmed value and normal operation continues (step 408).

The operation of a pacemaker in accordance with this invention is illustrated by the traces of FIGS. 5–7 which have been generated by using a cardiac simulator and a Telectronics META 1254 pacemaker. In each of these FIGS., the top two traces indicate the main timing events for the pacemaker. The third trace indicates the internal ECG obtained and logged by the pacemaker. The fourth trace indicates the surface ECG. In all of the FIGS. the following parameters are used:

min pacing rate=70 bpm
AV delay=160 msec
PVARP=280 msec

Figure 5A:
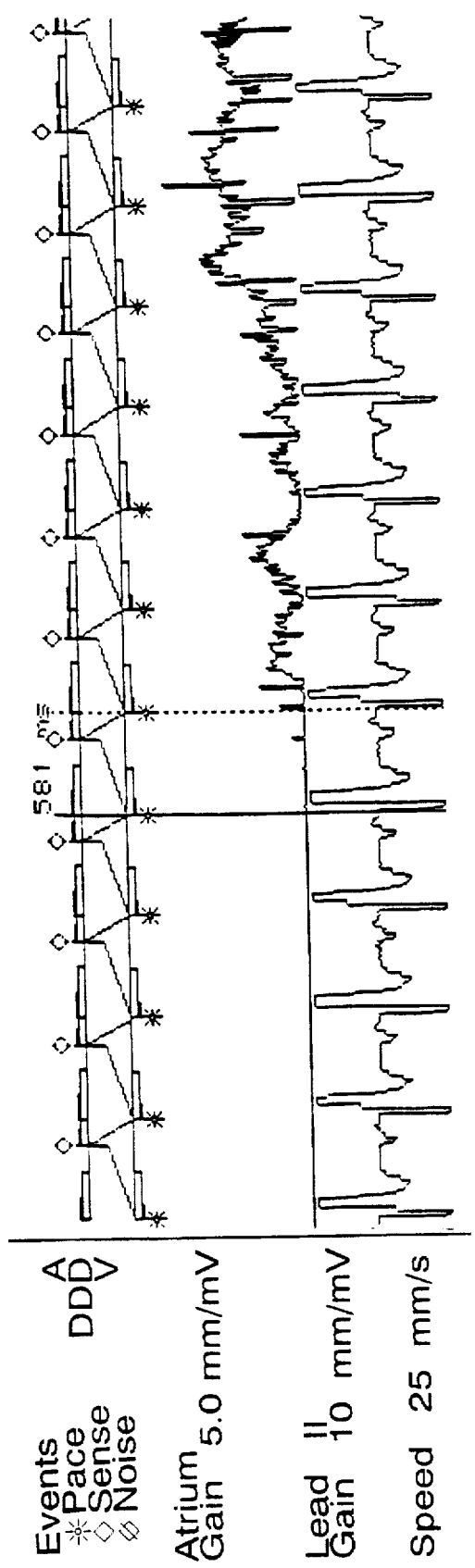
FIG. 5A–F shows a first set of atrial and ventricular signals.

In FIG. 5A the MTR is set to 120 ppm and the atrial rate from the heart simulator is 206 bpm. Every other atrial beat falls inside the postventricular atrial blanking period, but is not detected. The sensed cycle length is about twice the atrial interval from the heart simulator (291 ms). The resulting ventricular tracking rate is 103 ppm. Therefore, the conditions set for criteria (2) defined above has been met and the confirmation process of FIG. 10 is started by reducing MTR.

Figures 1, 5B:
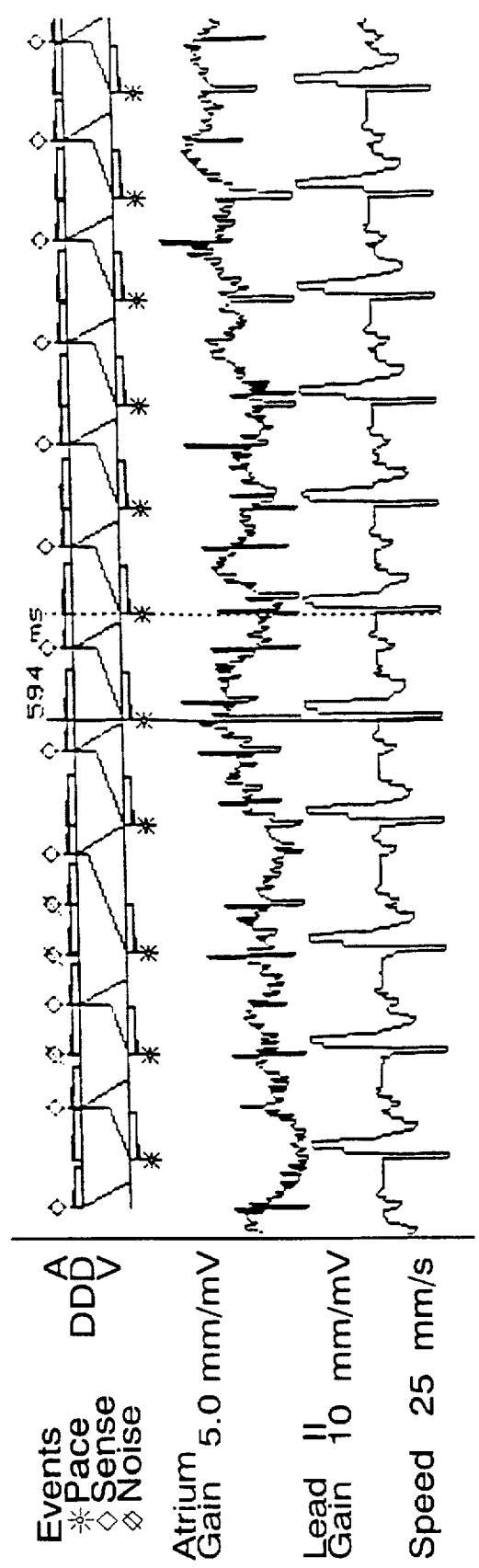
Figures 2, 5B:
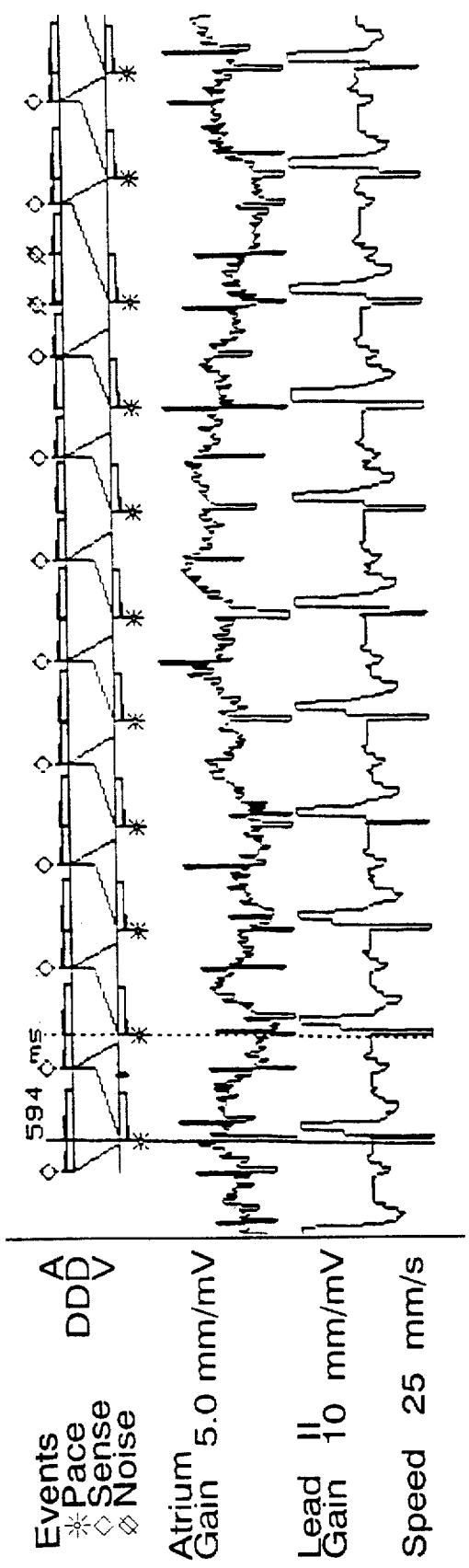
Figure 5C:
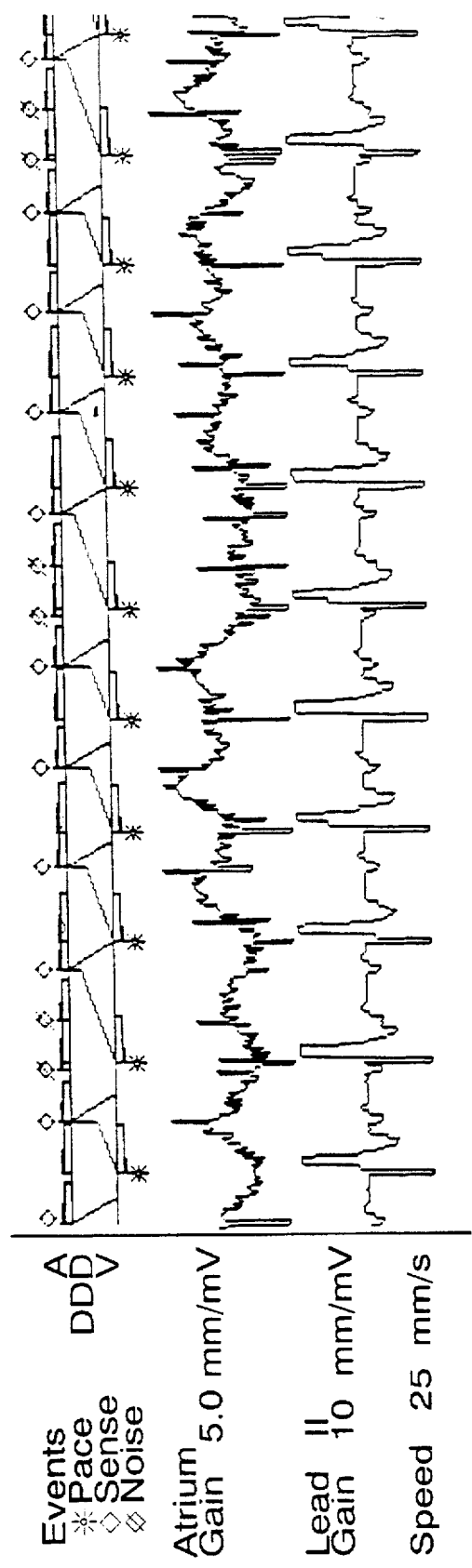
Figure 5D:
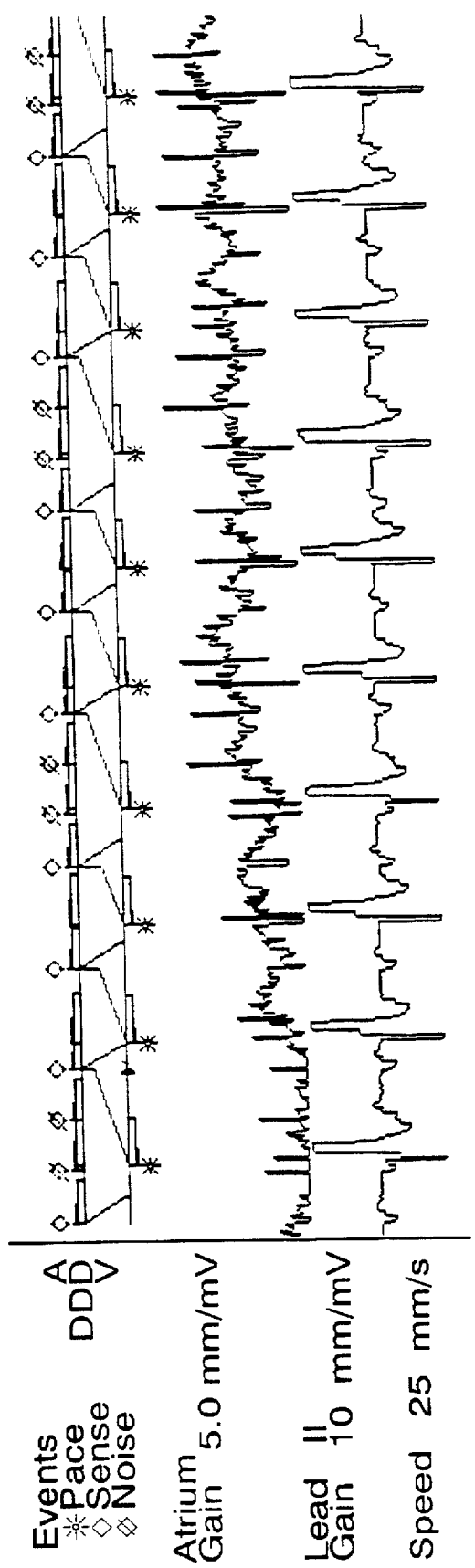
Figure 5E:
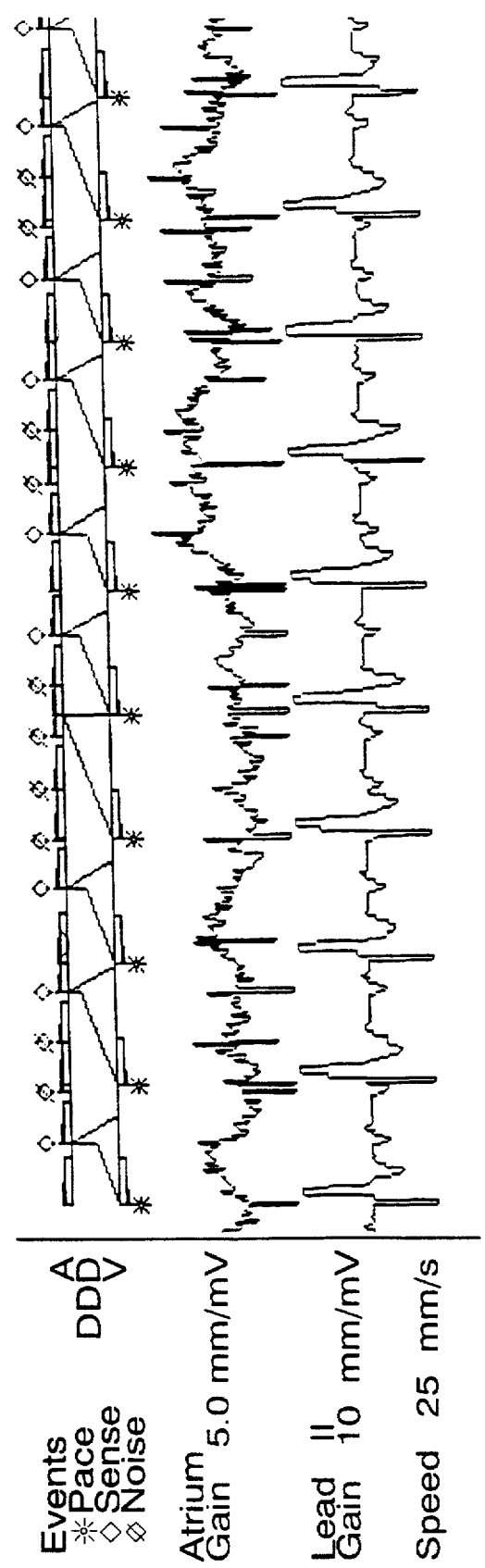
Figure 5F:
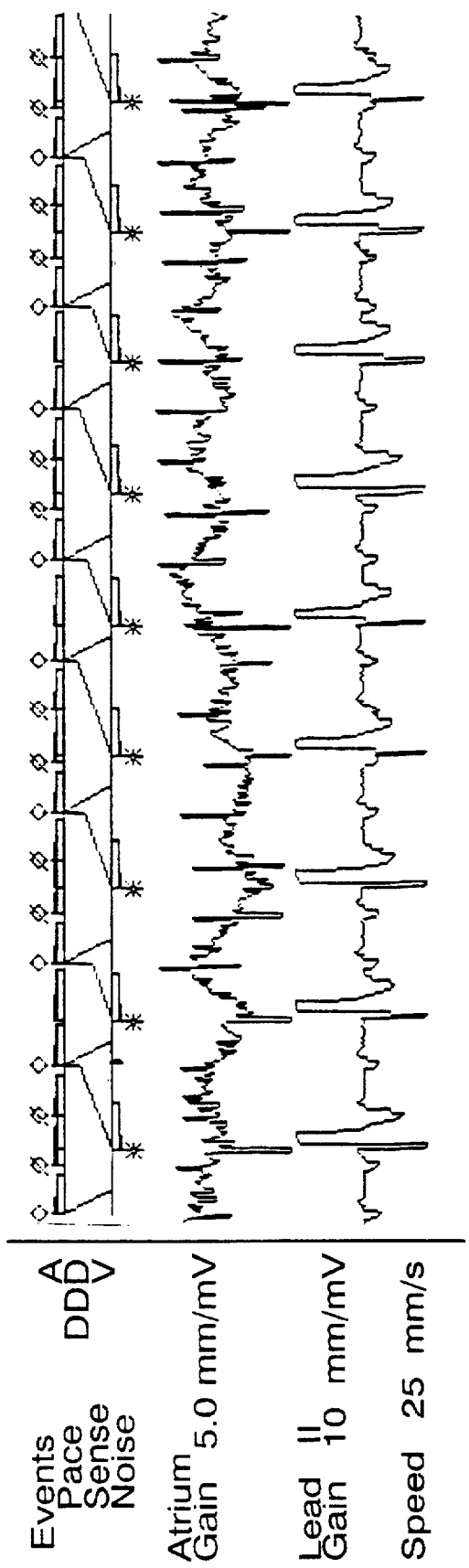

In FIGS. 5B1 and 5B2 (5B2 being the continuation of 5B1), the MTR has been reduced to 100 ppm and a pattern of some long intervals and some short intervals (5 short - 9 long - 3 short) is observed. In FIG. 5C, the MTR is reduced further to 95 ppm, and a pattern of 3 long, then 3 short intervals is observed. (Some intermediary steps have been omitted between 5A and 5B1/5B2). In FIG. 5D, the MTR is further reduced to 90 ppm, and a pattern of 2 long, then 3 short intervals is observed. Similar patterns with increasing number of short intervals are observed in FIGS. 5E and 5F where the MTR is 85 ppm and 80 ppm, respectively.

Figure 6A:
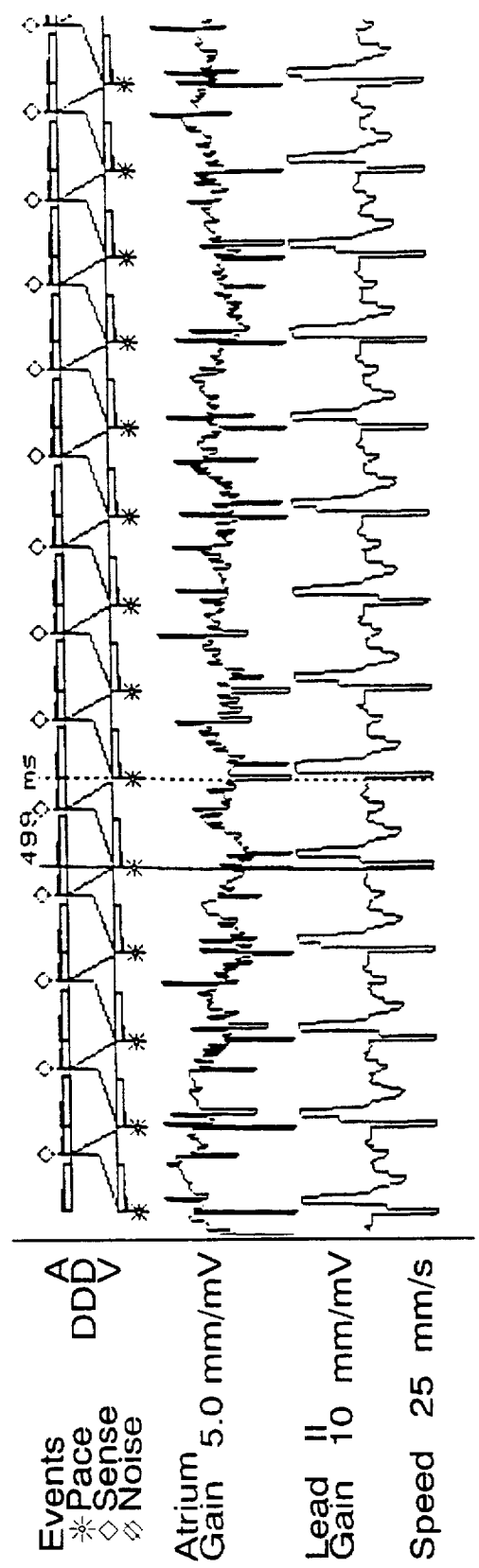
FIG. 6A–H shows a second set of atrial and ventricular signals.
Figure 6B:
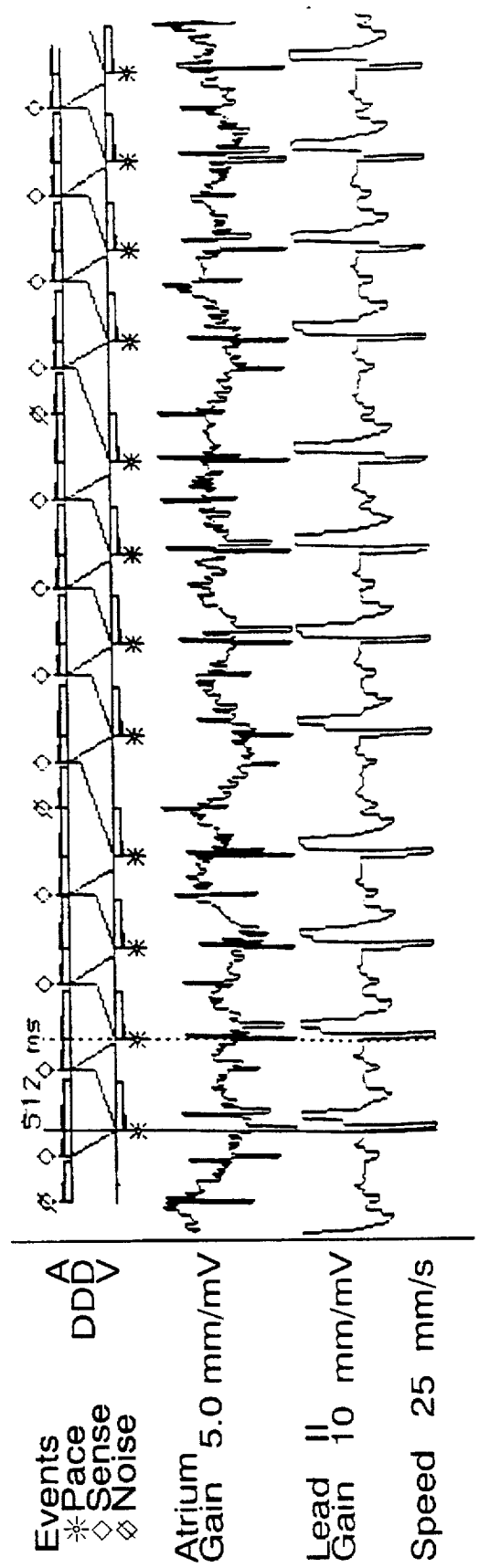
Figure 6C:
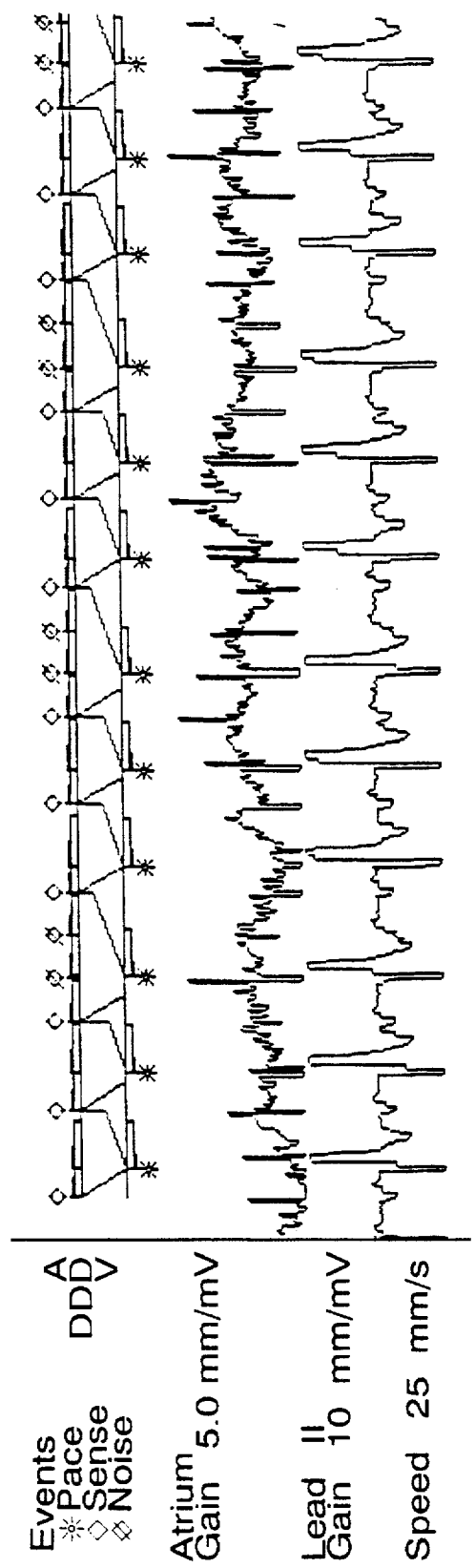
Figure 6D:
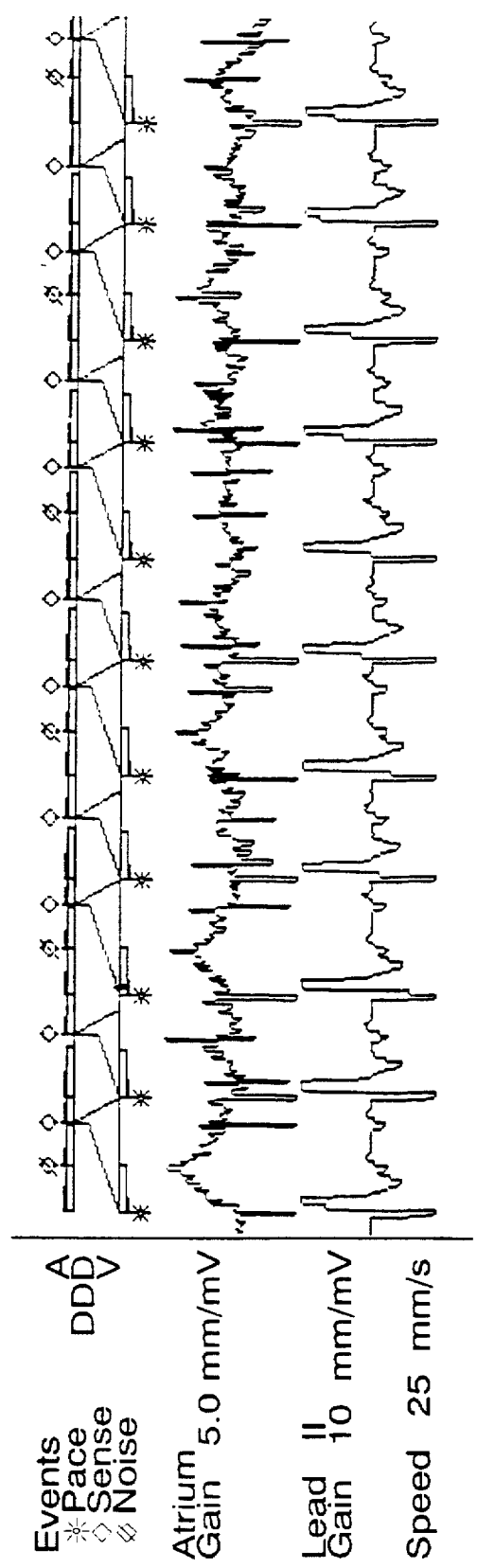
Figure 6E:
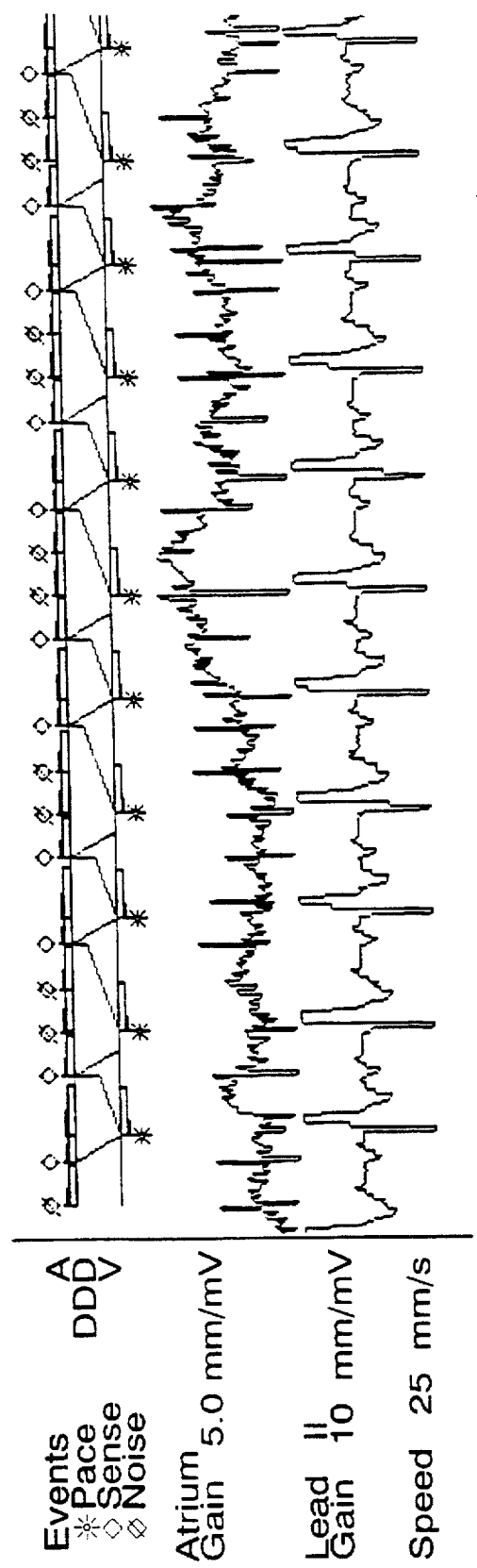

In FIGS. 6A–E, traces are shown for the atrial rate of 240 bpm. In FIG. 6A, every other atrial event is hidden. Patterns of some long intervals followed by some short intervals are observed in FIGS. 6B to 6E as the MTR is lowered gradually by 5 ppm at a time. By FIG. 6E the pattern LSSSLSSSLSSS . . . emerges. For comparison purposes, the same tests were repeated in FIGS. 6F–6I, but with an atrial rate of 120 bpm. As seen in these FIGS., this time the atrial intervals remained about the same, i.e., without L and S intervals.

Figure 6F:
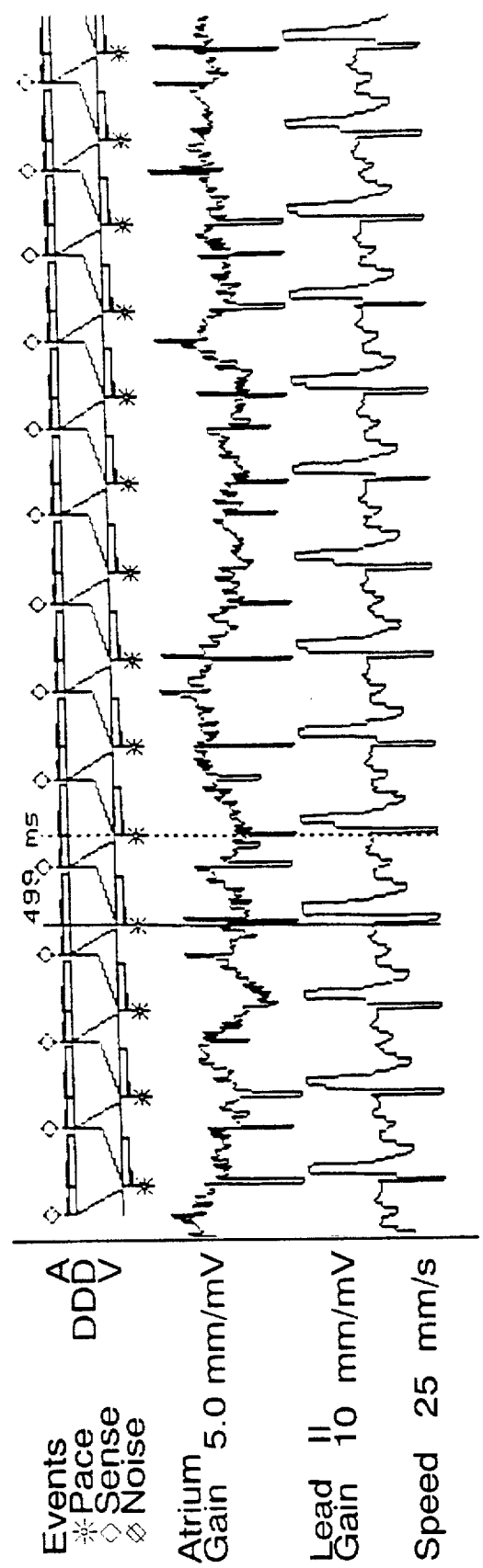
Figure 6G:
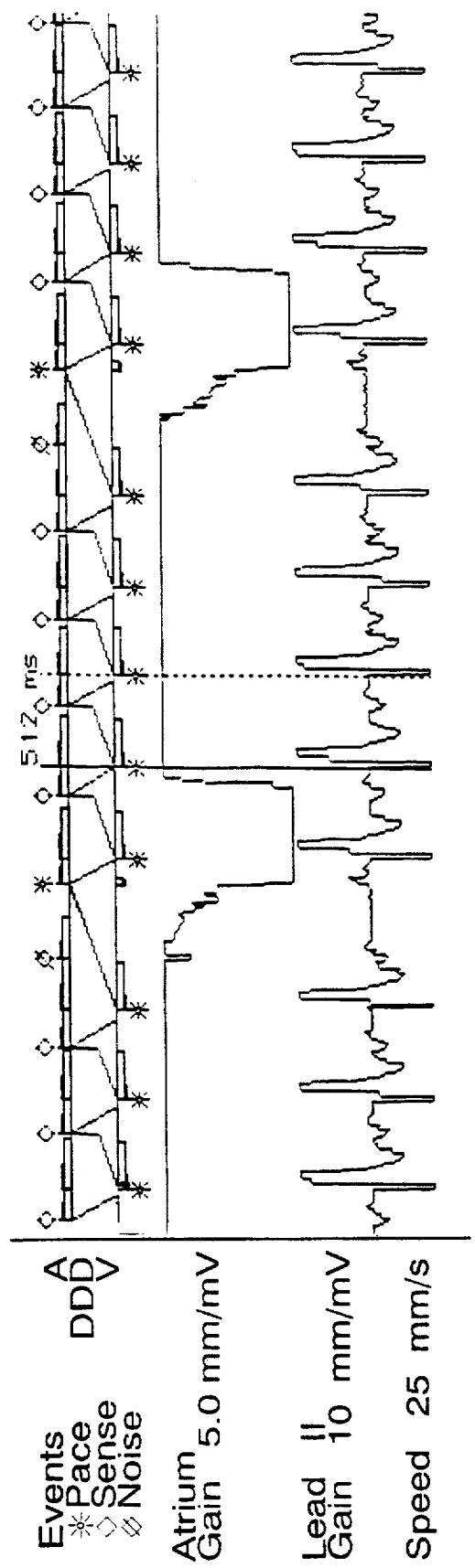
Figure 6H:
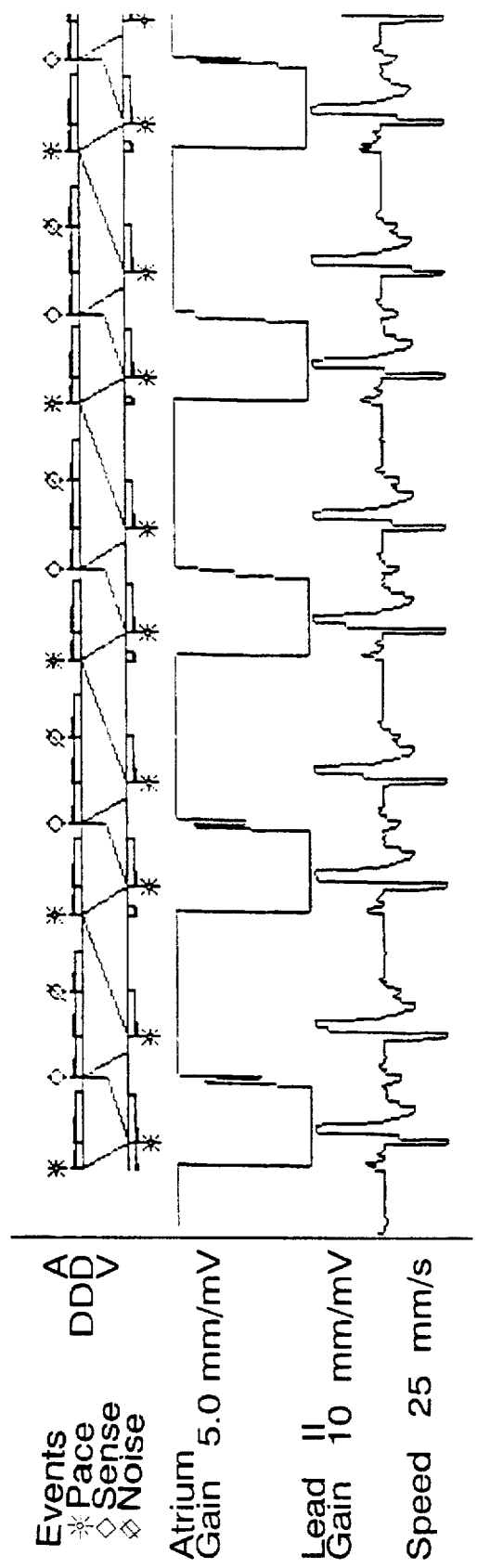
Figure 7A:
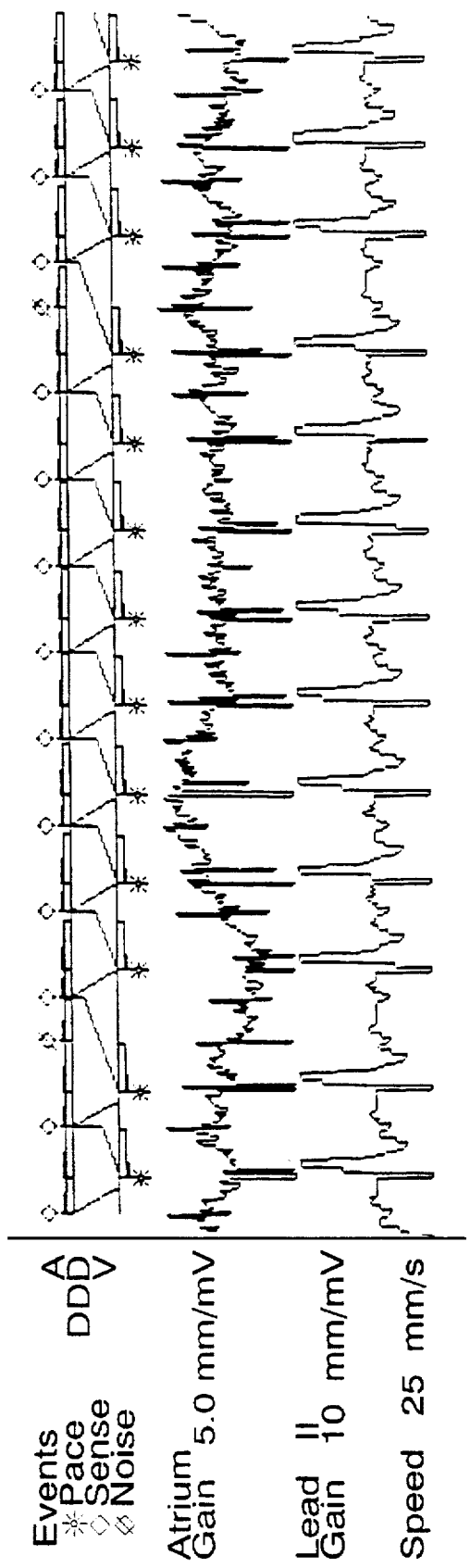
FIG. 7A–E shows a third set of atrial and ventricular signals.
Figure 7B:
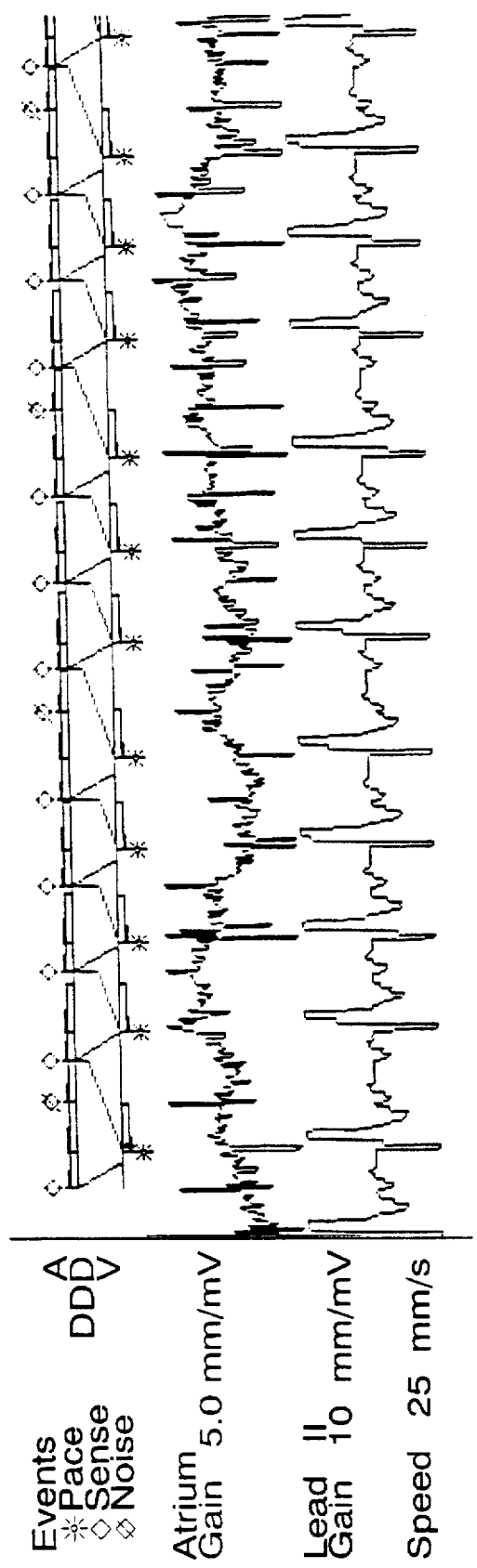
Figure 7C:
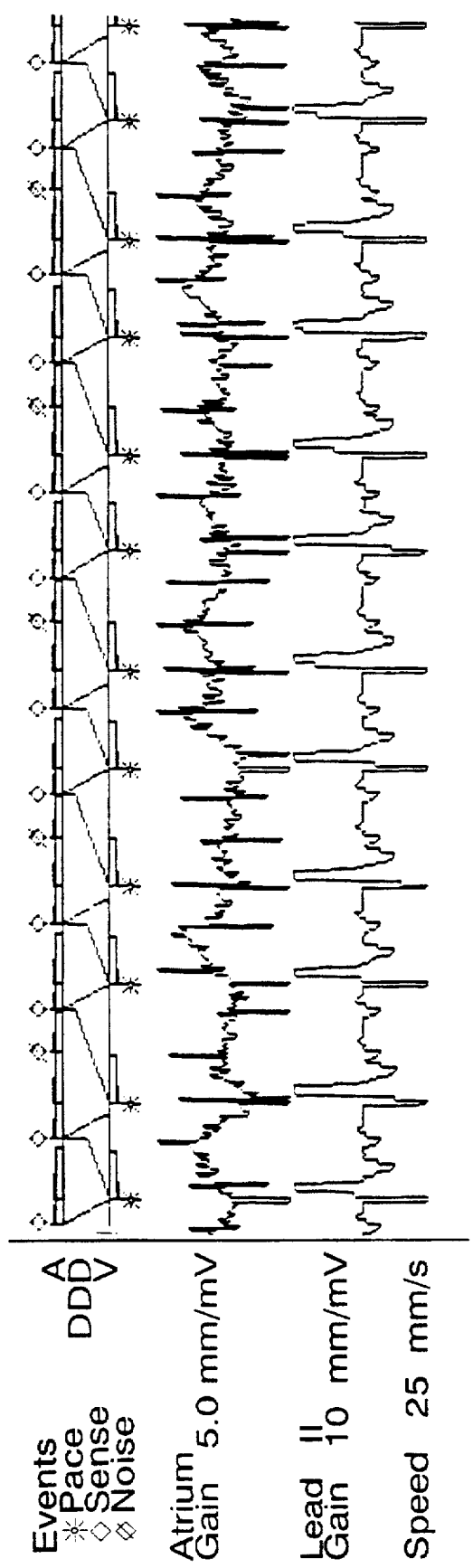
Figure 7D:
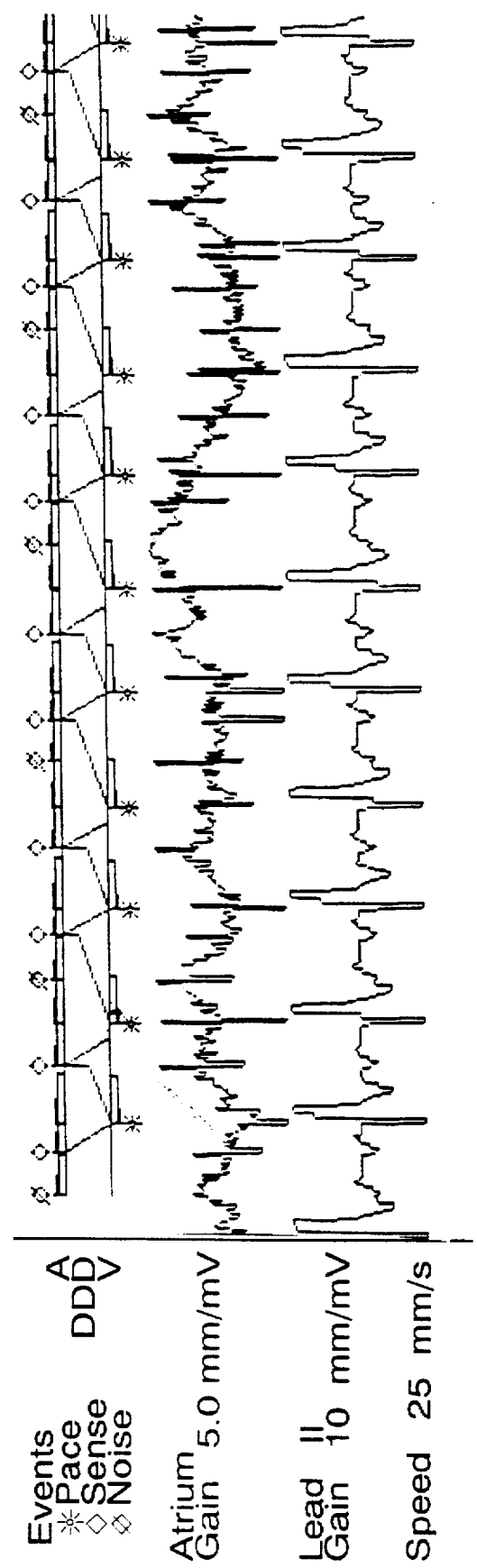
Figure 7E:
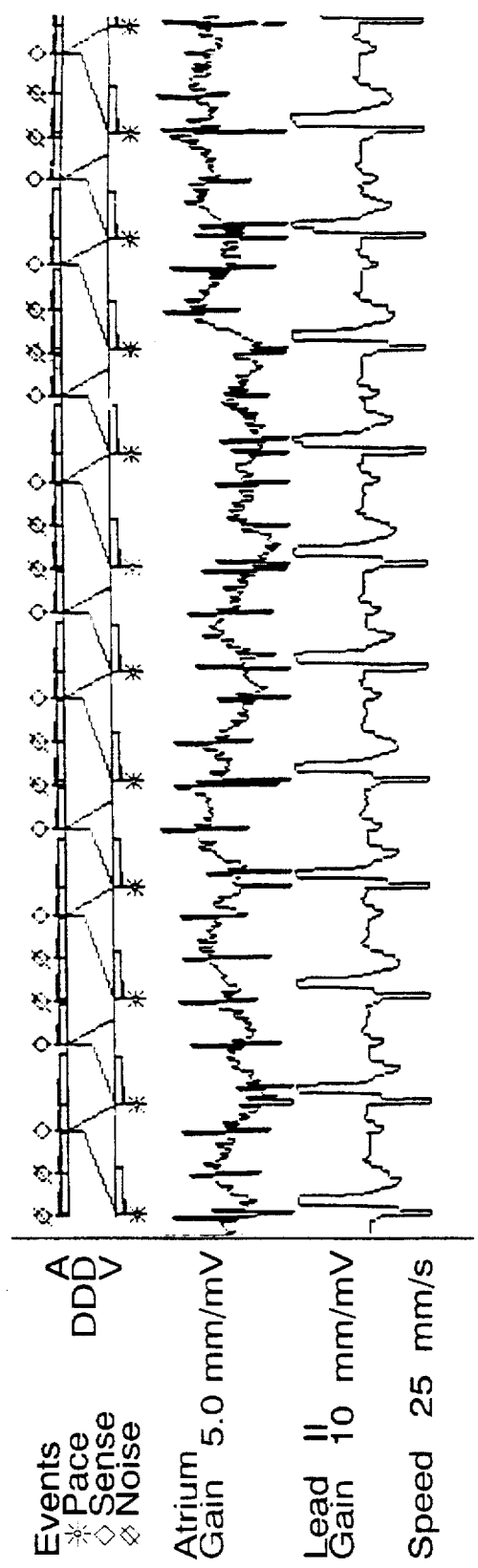

In FIG. 7A, the same initial conditions are used as in FIGS. 5A, 6A and 6F except that the atrial rate is set to 242 bpm. A few short intervals are observed. Between each long interval, there is hidden atrial event. As MTR is decreased by 5 ppm, a pattern of short and long intervals is immediately apparent. In FIG. 7B the pattern is LLLSLLLS. In FIG. 7D (at 105 ppm) the pattern is LLSLLSLSS... In FIG. 7E (at MTR=100 ppm) the pattern becomes SSSLSSSLSSSL...

Thus, as illustrated by the traces by reducing MTR patterns of short and long intervals are revealed thus confirming atrial tachyarrhythmia.

The advantages of the above-described method for detecting atrial tachycardias include: (1) it allows more accurate AMS operations when a stable atrial tachyarrhythmia with hidden senses, which may not be detected by the prior art AMS implementations, (2) a gradually reducing ventricular rate to the sensor indicated rate before AMS, and (3) intermittent AMS operation is avoided.

Figure 13:
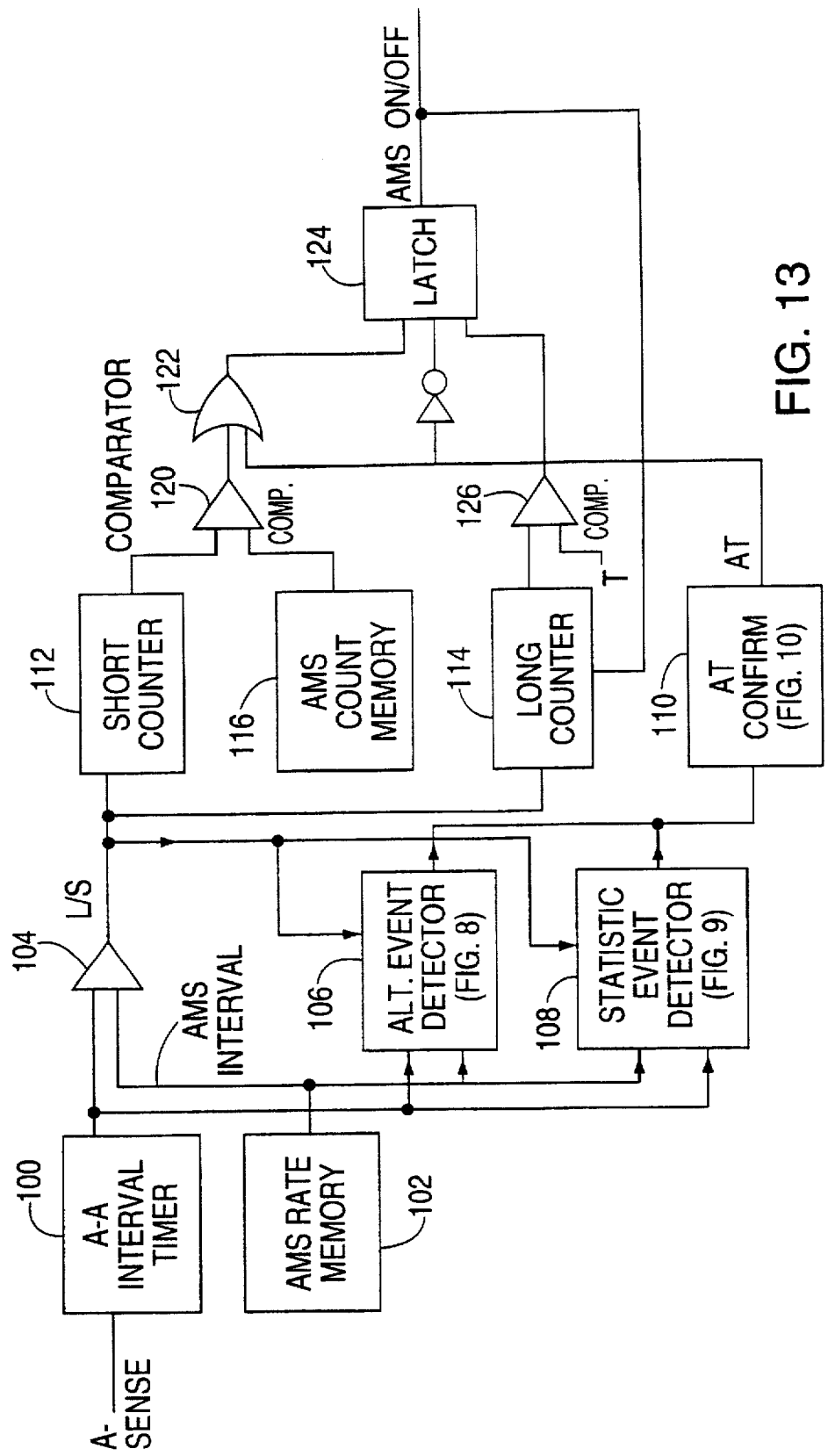
FIG. 13 shows a schematic diagram for an alternate embodiment of the invention.

Details of the AMS controller 80 are shown in FIG. 13. Controller 80 includes an A—A interval timer 100 for counting the A—A intervals based on the A-sense signals. A memory 102 is used to store the AMS RATE parameter. This interval and the corresponding AMS interval are fed to a comparator 104 which then determines whether each A—A interval is a long or a short interval (line L/S). This information, as well as the A—A interval and the AMS interval, are fed to the alternate event detector 106 which performs the operation described in FIG. 8, and to a statistical event detector 108 which performs the operation described in FIG. 9. The outputs of the detectors 106 and 108 are fed to the atrial tachycardia, confirm circuit 110 which performs the operation described in FIG. 10. The output of this circuit 110 indicates that atrial tachyarrhythmia has been detected.

As previously mentioned, in prior art pacemakers, symmetrical counters (one long or short interval) decreases/increases the counter by '1' are used for atrial tachyarrhythmia detection. Instead of symmetrical counters, the present invention makes use of two asymmetric counters 112, 114 for AMS detection to accommodate sensing problems such as undersensing during atrial fibrillation or hidden atrial sensed events during a stable atrial tachyarrhythmia and to avoid frequent mode switching. In FIG. 13 both approaches are illustrated, i.e., asymmetrical counters 112, 114 and the atrial tachycardia detection; and confirmation approach performed by detectors 106, 108, and circuit 110, it is being understood that either approach may be used as well.

The basic concept of the asymmetrical approach is to have different numbers of short and long intervals to increment or decrement the counters. For example, in FIG. 13, a short counter 112 is used to count short pulses and a counter 114 is used to count long pulses as follows.

Initially, when the pacemaker is operating in its normal responsive mode and AMS is OFF, every short atrial interval indicated on line L/S increments the short interval counter 112. However, it takes three, rather than one, long intervals to decrement the short counter 112 by '1'. The short interval counter counts up to the programmed AMS Count, stored in memory. The output of counter 112 and memory 116 are compared by comparator 120. If the count in counter 112 exceeds the AMS count, the comparator 120 generates an output which is fed to an OR gate 122. Another input of the OR gate 122 is connected to the atrial tachycardia AT confirm circuit 110. If either of its inputs goes high, the output of OR gate 122 goes high, thereby switching a latch 124 on. Latch 124 then generates an AMS ON signal to enable the AMS feature.

After the AMS ON is generated, the long interval counter 114 is activated. Three long intervals on line L/S increment the long interval counter 114 but every short interval decrements the long interval counter 114. The output of the counter 114 is fed to a comparator 126 which compares this output to a threshold level T. When the long interval counter 114 reaches threshold T (which may be preset in the range of 3–5) or no atrial event is sensed for a number of seconds (e.g., 5–10 seconds, during which period VVV/VVIR pacing is applied), latch 124 is turned off, the AMS OFF signal is enabled and dual chamber operation resumes.

The advantages of this latter algorithm are: (1) faster enabling of the AMS mode during under-sensed atrial tachyarrhythmias, (2) avoidance of intermittent mode switching, (3) use of current up/down counters presently available in the current AMS algorithm.

Although the invention has been described with reference to several particular embodiments, it is to be understood that these embodiments are merely illustrative of the application of the principles of the invention. Accordingly, the embodiments described in particular should be considered exemplary, not limiting, with respect to the following claims.

I claim:

1. An implantable pacemaker comprising:

an atrial sensor sensing intrinsic atrial events and generating atrial signals;

a ventricular sensor sensing intrinsic ventricular events and generating ventricular signals;

a pacing generator for generating pacing pulses for the patient's heart in response to pacing commands;

a controller receiving said atrial and ventricular signals and generating said pacing commands;

a timer for generating blanking periods during which said atrial signals are not received by said controller; and an atrial tachycardia detector receiving said atrial and ventricular signals, said detector generating a tachycardia signal indicative of a tachycardia condition of said patient by measuring the intervals between said atrial signals and determining if any of said atrial signals fall within said blanking periods.

2. The pacemaker of claim 1 wherein said controller is arranged and constructed to receive said atrial tachycardia signal and in response to adjust a timing of said command signals.

3. The pacemaker of claim 1 further comprising a metabolic demand sensor sensing a metabolic demand of said patient, said metabolic demand generating a corresponding demand parameter.

4. The pacemaker of claim 3 wherein said controller is adapted to receive said demand parameter and to adjust a timing of said pacing commands in response to said demand parameter.

5. The pacemaker of claim 4 further comprising a selector for selecting a first mode and a second mode for said controller, wherein said controller is adapted in said first mode to generate said command signals in accordance with said demand parameter and wherein in said second mode said controller is adapted to generate said command signals at intervals independent of said demand parameter.

6. The pacemaker of claim 5 wherein said selector is adapted to select said second mode in response to said atrial tachycardia signal.

7. A dual chamber implantable pacemaker comprising:

an atrial sensor sensing intrinsic atrial events and generating atrial signals;

a ventricular sensor sensing intrinsic ventricular events and generating ventricular signals;

an atrial pulse generator for generating atrial pulses in response to pacing commands;

a ventricular pulse generator for generating ventricular pulses in response to pacing commands;

a demand sensor for sensing a demand of said patient and generating a demand parameter;

a controller receiving said atrial and ventricular signals and said demand parameter and generating corresponding pacing commands;

a timer generating blanking atrial and ventricular periods during which some of the corresponding atrial and ventricular signals are masked from said controller; and an atrial tachycardia detector receiving said atrial signals, said detector analyzing said atrial signals to determine when some of said atrial signals are masked by said blanking periods to indicate a tachycardia condition.

8. The pacemaker of claim 7 wherein during said atrial tachycardia condition, the atrial signals received by said controller are defined by atrial pulses separated by a set of short and a set of long atrial intervals, said detector including an analyzer for analyzing a pattern of said short and long atrial intervals.

9. The pacemaker of claim 8 wherein said detector is adapted to generate said atrial tachycardia signal in the presence of a pattern of alternate short and long atrial intervals.

10. The pacemaker of claim 9 further comprising a verifier coupled to said atrial tachycardia detector and is adapted to verify said atrial tachycardia condition.

11. The pacemaker of claim 7 wherein detector is adapted to compare said intervals to a pacing parameter and to generate said atrial tachycardia signal if said intervals are within a preselected range defined in accordance with said pacing parameter.

12. The pacemaker of claim 7 wherein said pattern of short and long intervals is dependent on a pacing parameter for operating said controller, wherein said controller is adapted to chance said pacing parameter and said detector is adapted to analyze the corresponding patterns.

13. The pacemaker of claim 7 further comprising a mode selector for selecting a mode of operation of said controller in accordance with said atrial tachycardia signal.

14. The pacemaker of claim 7 wherein said controller is adapted to operate in a first and a second mode of operation, wherein in said first mode of operation said controller is adapted to generate said pacing commands in accordance with said demand parameter and wherein in said second mode said pacing commands are generated by said controller independently of said demand parameter.

15. A method of detecting atrial tachycardia in a patient with an implantable pacemaker adapted to operate in a first mode in which said pacemaker is responsive to a metabolic demand and a second mode in which said pacemaker is adapted to operate independently of said metabolic demand, comprising the steps of:

detecting intrinsic atrial events and generating in response atrial signals;

generating blanking periods, during an atrial tachycardia some of said atrial events being masked by said blanking periods;

detecting said metabolic demand of said patient;

detecting said atrial tachycardia condition by analyzing the intervals between said atrial signals and determining from said intervals whether any atrial signals have been masked by said blanking periods;

generating command signals corresponding to said atrial signals and said metabolic demand in said first mode in the absence of said atrial tachycardia; and generating command signals for said second mode in the presence of said atrial tachycardia signal.

16. The method of claim 15 wherein said step of detecting said atrial tachycardia condition includes a step of identifying a pattern of said intervals, said pattern being characteristic of said atrial tachycardia.

17. The method of claim 15 further comprising the step of verifying said atrial tachycardia condition before generating commands for said second mode.

18. The method of claim 17 wherein said step of verifying includes varying a pacing parameter.

19. The method of claim 18 further comprising analyzing said pattern to detect said atrial tachycardia.

20. The method of claim 19 further comprising the step of changing said pacing parameter and analyzing the resulting patterns.

21. The method of claim 20 wherein said step of changing comprises reducing said pacing parameter from a top value.

22. The method of claim 21 wherein said step of changing comprises reducing a maximum ventricular rate.

* * * * *